United States Patent
Sogabe et al.

(10) Patent No.: US 9,816,996 B2
(45) Date of Patent: Nov. 14, 2017

(54) ANTIBODY FOR DETECTING EPITHELIAL OVARIAN CANCER MARKER AND METHOD FOR DIAGNOSING EPITHELIAL OVARIAN CANCER

(75) Inventors: Maki Sogabe, Ibaraki (JP); Tomomi Kubota, Ibaraki (JP); Akira Togayachi, Ibaraki (JP); Yuzuru Ikehara, Ibaraki (JP); Hisashi Narimatsu, Ibaraki (JP); Hiromichi Sawaki, Ibaraki (JP); Hayao Nakanishi, Nagoya (JP); Toru Nakanishi, Nagoya (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 14/234,783

(22) PCT Filed: Jul. 26, 2012

(86) PCT No.: PCT/JP2012/068980
§ 371 (c)(1),
(2), (4) Date: Jan. 24, 2014

(87) PCT Pub. No.: WO2013/015363
PCT Pub. Date: Jan. 31, 2013

(65) Prior Publication Data
US 2014/0295455 A1 Oct. 2, 2014

(30) Foreign Application Priority Data
Jul. 26, 2011 (JP) .................................. 2011-163299

(51) Int. Cl.
*G01N 33/574* (2006.01)
*C12N 5/16* (2006.01)
*C07K 16/30* (2006.01)
*C07K 16/40* (2006.01)

(52) U.S. Cl.
CPC ... *G01N 33/57449* (2013.01); *C07K 16/3069* (2013.01); *C07K 16/40* (2013.01); *C12N 5/163* (2013.01)

(58) Field of Classification Search
None
See application file for complete search history.

(56) References Cited

U.S. PATENT DOCUMENTS

| | | | |
|---|---|---|---|
| 6,258,540 B1 * | 7/2001 | Lo .................. | C12Q 1/6879 435/440 |
| 6,355,623 B2 * | 3/2002 | Seidman et al. ................. | 514/45 |
| 7,005,279 B1 * | 2/2006 | Sasaki .................. | C12N 9/1085 435/193 |
| 2004/0203111 A1 * | 10/2004 | Schwientek et al. ........ | 435/69.1 |
| 2005/0037389 A1 * | 2/2005 | Santin .................. | C12Q 1/6886 435/6.18 |
| 2005/0255489 A1 * | 11/2005 | Pierce .................. | C12N 9/1051 435/6.11 |
| 2006/0030001 A1 | 2/2006 | Sasaki et al. | |
| 2008/0113874 A1 | 5/2008 | Bunn et al. | |
| 2011/0306049 A1 | 12/2011 | Yamashita et al. | |
| 2014/0242607 A1 * | 8/2014 | Sogabe ............ | G01N 33/57449 435/7.4 |

FOREIGN PATENT DOCUMENTS

| | | |
|---|---|---|
| EP | 0445750 | 9/1991 |
| JP | 03-259093 | 11/1991 |
| WO | 2009/028417 A1 | 3/2009 |

OTHER PUBLICATIONS

Janeway et al. (Immunobiology 5, 2001, p. 100-101).*
Rudikoff et al. (PNAS USA, 1982, 79: 1979-1983).*
Gussow et al. (1991, Methods in Enzymology 203:99-121).*
MacCallum et al. (J. Mol. Biol. (1996) 262, 732-745).*
Boyd (The Basic Science of Oncology, 1992, McGraw-Hill, Inc., p. 379).*
Hornbeck et al. (Current Protocols in Mol. Biol. Enzyme-Linked Immunosorbent Assays (ELISA) 2000, 11.2.1-11.2.22).*
Di Virgillio et al. (Glycobiology 1999 9(4): 353-364).*
Yanagi et al. (J. Gastroenterology and Hepatology 2001 16:1282-1289).*
Bast, Robert C., Jr., et al. "A Radioimmunoassay Using a Monoclongal Antibody to Monitor the Course of Epithelial Ovarian Cancer", The New England Journal of Medicine, Oct. 13, 1983, vol. 309, No. 15, pp. 883-887.
Susuki, Mitsuaki, et al., "Clinical Value of a New Serum Tumor Marker CA602 in Ovarian Cancers", Journal of Japan Society for Cancer Therapy, Jul. 1990, vol. 25, No. 7, pp. 1454-1460 (with English Abstract).
Inaba, Noriyuki, et al., "A Fundamental and Clinical Investigation of Cancer Antigen 130 (CA130) in the Field of Obstetrics and Gynecology", Journal of Japan Society for Cancer Therapy, Oct. 1989, vol. 24, No. 10, pp. 2426-2435 (with partial English translation).
Ohuchi, Noriaki, et al., "Levels of Circulating Tumor-Associated Glycoprotein (TAG-72) in Patients with Carcinoma Using a Novel Tumor Marker, CA72-4", Japanese Journal of Cancer and Chemotherapy, Sep. 1988, vol. 15, No. 9, pp. 2767-2772 (with partial English translation including English abstract).
Nozawa, Shiro, et al., "Applications of Tumor Markers to the Screening of Endometrial and Ovarian Cancers", 1996, vol. 54 pp. 1665-1673 (with English abstract).

(Continued)

*Primary Examiner* — Peter J Reddig
(74) *Attorney, Agent, or Firm* — McCarter & English, LLP

(57) ABSTRACT

The present invention provides an antibody capable of specifically recognizing and detecting the highly specific cancer marker with respect to the epithelial ovarian cancer, or a fragment of the antibody. The present invention provides an anti-β1,3-N-acetylglucosaminyltransferase 3 antibody for diagnosis of epithelial ovarian cancer, i.e., an antibody for detection of a glycosyltransferase β1,3-N-acetylglucosaminyltransferase 3 as an epithelial ovarian cancer marker. The antibody recognizes, as an epitope, a part of a polypeptide of the enzyme consisting of the amino acid sequence represented by SEQ ID NO: 1.

6 Claims, 9 Drawing Sheets

(56) References Cited

OTHER PUBLICATIONS

Charpin, Colette, et al., "Carcinoembryonic Antigen (CEA) and Carbohydrate Determinant 19-9 (CA 19-9) Localization in 121 Primary and Metastatic Ovarian Tumors: An Immunohistochemical Study with the Use of Monoclonal Antibodies", International Journal of Gynecological Pathology, 1982, vol. 1, No. 3, pp. 231-245.
Konica Minolta, Inc., "GAT Test Kit for Determination of the Serum GAT Level by EIA", Oct. 2003, Instructions for Use, pp. 1-6 (with partial English translation).
Seko, Akira, et al., "b1,3-Galactosyltransferases-4/5 are Novel Tumor Markers for Gynecological Cancers", Tumor Biology, 2009, vol. 30, pp. 43-50.
Shiraishi, Norihiko, et al., "Identification and Characterization of Three Novel b1,3-N-Acetylglucosaminyltransferases Structurally Related to the b1,3-Galactosyltransferase Family", The Journal of Biological Chemistry, 2001, vol. 276, No. 5, pp. 3498-3507.
International Preliminary Report on Patentability, dated Jan. 28, 2014, relating to International Application No. PCT/JP2012/068980.
Written Opinion of the International Searching Authority, dated Sep. 4, 2012 relating to International Application No. PCT/JP2012/068980.
Nozawa, Shiro, et al., "Applications of Tumor Markers to the Screening of Endometrial and Ovarian Cancers", Japanese Journal of Clinical Medicine, 1996, vol. 54, pp. 1665-1673 (with English abstract).
Supplementary European Search Report dated Feb. 27, 2015, based on foreign counterpart; European Application No. EP12818196—2 Pages.

\* cited by examiner a b c

SEQUENCE LISTING

```
<160> NUMBER OF SEQ ID NOS: 9

<210> SEQ ID NO 1
<211> LENGTH: 335
<212> TYPE: PRT
<213> ORGANISM: Homo sapiens

<400> SEQUENCE: 1

Glu Gln Pro Pro Ala Ile Pro Glu Ala Leu Ala Trp Pro Thr Pro Pro
1               5                   10                  15

Thr Arg Pro Ala Pro Ala Pro Cys His Ala Asn Thr Ser Met Val Thr
            20                  25                  30

His Pro Asp Phe Ala Thr Gln Pro Gln His Val Gln Asn Phe Leu Leu
        35                  40                  45

Tyr Arg His Cys Arg His Phe Pro Leu Leu Gln Asp Val Pro Pro Ser
    50                  55                  60

Lys Cys Ala Gln Pro Val Phe Leu Leu Val Ile Lys Ser Ser Pro
65                  70                  75                  80

Ser Asn Tyr Val Arg Arg Glu Leu Leu Arg Arg Thr Trp Gly Arg Glu
                85                  90                  95

Arg Lys Val Arg Gly Leu Gln Leu Arg Leu Leu Phe Leu Val Gly Thr
            100                 105                 110

Ala Ser Asn Pro His Glu Ala Arg Lys Val Asn Arg Leu Leu Glu Leu
        115                 120                 125

Glu Ala Gln Thr His Gly Asp Ile Leu Gln Trp Asp Phe His Asp Ser
    130                 135                 140

Phe Phe Asn Leu Thr Leu Lys Gln Val Leu Phe Leu Gln Trp Gln Glu
145                 150                 155                 160

Thr Arg Cys Ala Asn Ala Ser Phe Val Leu Asn Gly Asp Asp Val
                165                 170                 175

Phe Ala His Thr Asp Asn Met Val Phe Tyr Leu Gln Asp His Asp Pro
            180                 185                 190

Gly Arg His Leu Phe Val Gly Gln Leu Ile Gln Asn Val Gly Pro Ile
        195                 200                 205

Arg Ala Phe Trp Ser Lys Tyr Tyr Val Pro Glu Val Val Thr Gln Asn
    210                 215                 220

Glu Arg Tyr Pro Pro Tyr Cys Gly Gly Gly Phe Leu Leu Ser Arg
225                 230                 235                 240

Phe Thr Ala Ala Ala Leu Arg Arg Ala His Val Leu Asp Ile Phe
                245                 250                 255
```

```
Pro Ile Asp Asp Val Phe Leu Gly Met Cys Leu Glu Leu Glu Gly Leu
            260                 265                 270

Lys Pro Ala Ser His Ser Gly Ile Arg Thr Ser Gly Val Arg Ala Pro
            275                 280                 285

Ser Gln His Leu Ser Ser Phe Asp Pro Cys Phe Tyr Arg Asp Leu Leu
            290                 295                 300

Leu Val His Arg Phe Leu Pro Tyr Glu Met Leu Leu Met Trp Asp Ala
305                 310                 315                 320

Leu Asn Gln Pro Asn Leu Thr Cys Gly Asn Gln Thr Gln Ile Tyr
                325                 330                 335

<210> SEQ ID NO 2
<211> LENGTH: 372
<212> TYPE: PRT
<213> ORGANISM: Homo sapiens

<400> SEQUENCE: 2

Met Lys Tyr Leu Arg His Arg Arg Pro Asn Ala Thr Leu Ile Leu Ala
1               5                   10                  15

Ile Gly Ala Phe Thr Leu Leu Leu Phe Ser Leu Leu Val Ser Pro Pro
            20                  25                  30

Thr Cys Lys Val Gln Glu Gln Pro Ala Ile Pro Glu Ala Leu Ala
            35                  40                  45

Trp Pro Thr Pro Pro Thr Arg Pro Ala Pro Ala Pro Cys His Ala Asn
            50                  55                  60

Thr Ser Met Val Thr His Pro Asp Phe Ala Thr Gln Pro Gln His Val
65                  70                  75                  80

Gln Asn Phe Leu Leu Tyr Arg His Cys Arg His Phe Pro Leu Leu Gln
                85                  90                  95

Asp Val Pro Pro Ser Lys Cys Ala Gln Pro Val Phe Leu Leu Leu Val
            100                 105                 110

Ile Lys Ser Ser Pro Ser Asn Tyr Val Arg Arg Glu Leu Leu Arg Arg
            115                 120                 125

Thr Trp Gly Arg Glu Arg Lys Val Arg Gly Leu Gln Leu Arg Leu Leu
            130                 135                 140

Phe Leu Val Gly Thr Ala Ser Asn Pro His Glu Ala Arg Lys Val Asn
145                 150                 155                 160

Arg Leu Leu Glu Leu Glu Ala Gln Thr His Gly Asp Ile Leu Gln Trp
                165                 170                 175

Asp Phe His Asp Ser Phe Phe Asn Leu Thr Leu Lys Gln Val Leu Phe
            180                 185                 190

Leu Gln Trp Gln Glu Thr Arg Cys Ala Asn Ala Ser Phe Val Leu Asn
            195                 200                 205

Gly Asp Asp Asp Val Phe Ala His Thr Asp Asn Met Val Phe Tyr Leu
            210                 215                 220

Gln Asp His Asp Pro Gly Arg His Leu Phe Val Gly Gln Leu Ile Gln
225                 230                 235                 240

Asn Val Gly Pro Ile Arg Ala Phe Trp Ser Lys Tyr Tyr Val Pro Glu
                245                 250                 255

Val Val Thr Gln Asn Glu Arg Tyr Pro Pro Tyr Cys Gly Gly Gly
            260                 265                 270

Phe Leu Leu Ser Arg Phe Thr Ala Ala Leu Arg Arg Ala Ala His
            275                 280                 285

Val Leu Asp Ile Phe Pro Ile Asp Asp Val Phe Leu Gly Met Cys Leu
```

```
                290                 295                 300
Glu Leu Glu Gly Leu Lys Pro Ala His Ser Gly Ile Arg Thr Ser
305                 310                 315                 320

Gly Val Arg Ala Pro Ser Gln His Leu Ser Ser Phe Asp Pro Cys Phe
                325                 330                 335

Tyr Arg Asp Leu Leu Val His Arg Phe Leu Pro Tyr Glu Met Leu
                340                 345                 350

Leu Met Trp Asp Ala Leu Asn Gln Pro Asn Leu Thr Cys Gly Asn Gln
                355                 360                 365

Thr Gln Ile Tyr
            370

<210> SEQ ID NO 3
<211> LENGTH: 740
<212> TYPE: PRT
<213> ORGANISM: Homo sapiens

<400> SEQUENCE: 3

Gly Asp Ser Pro Phe Thr Ile Arg Thr Glu Val Met Gly Gly Pro Glu
1               5                   10                  15

Ser Arg Gly Val Leu Arg Lys Met Ser Asp Leu Leu Glu Leu Met Val
                20                  25                  30

Lys Arg Met Asp Ala Leu Ala Arg Leu Glu Asn Ser Ser Glu Leu His
                35                  40                  45

Arg Ala Gly Gly Asp Leu His Phe Pro Ala Asp Arg Met Pro Pro Gly
            50                  55                  60

Ala Gly Leu Met Glu Arg Ile Gln Ala Ile Gln Asn Val Ser Asp
65                  70                  75                  80

Ile Ala Val Lys Val Asp Gln Ile Leu Arg His Ser Leu Leu Leu His
                85                  90                  95

Ser Lys Val Ser Glu Gly Arg Arg Asp Gln Cys Glu Ala Pro Ser Asp
                100                 105                 110

Pro Lys Phe Pro Asp Cys Ser Gly Lys Val Glu Trp Met Arg Ala Arg
            115                 120                 125

Trp Thr Ser Asp Pro Cys Tyr Ala Phe Phe Gly Val Asp Gly Thr Glu
    130                 135                 140

Cys Ser Phe Leu Ile Tyr Leu Ser Glu Val Glu Trp Phe Cys Pro Pro
145                 150                 155                 160

Leu Pro Trp Arg Asn Gln Thr Ala Ala Gln Arg Ala Pro Lys Pro Leu
                165                 170                 175

Pro Lys Val Gln Ala Val Phe Arg Ser Asn Leu Ser His Leu Leu Asp
                180                 185                 190

Leu Met Gly Ser Gly Lys Glu Ser Leu Ile Phe Met Lys Lys Arg Thr
            195                 200                 205

Lys Arg Leu Thr Ala Gln Trp Ala Leu Ala Ala Gln Arg Leu Ala Gln
    210                 215                 220

Lys Leu Gly Ala Thr Gln Arg Asp Gln Lys Gln Ile Leu Val His Ile
225                 230                 235                 240

Gly Phe Leu Thr Glu Glu Ser Gly Asp Val Phe Ser Pro Arg Val Leu
                245                 250                 255

Lys Gly Gly Pro Leu Gly Glu Met Val Gln Trp Ala Asp Ile Leu Thr
                260                 265                 270

Ala Leu Tyr Val Leu Gly His Gly Leu Arg Val Thr Val Ser Leu Lys
            275                 280                 285
```

-continued

```
Glu Leu Gln Ser Asn Leu Gly Val Pro Pro Gly Arg Gly Ser Cys Pro
290                 295                 300
Leu Thr Met Pro Leu Pro Phe Asp Leu Ile Tyr Thr Asp Tyr His Gly
305                 310                 315                 320
Leu Gln Gln Met Lys Arg His Met Gly Leu Ser Phe Lys Lys Tyr Arg
            325                 330                 335
Cys Arg Ile Arg Val Ile Asp Thr Phe Gly Thr Glu Pro Ala Tyr Asn
            340                 345                 350
His Glu Glu Tyr Ala Thr Leu His Gly Tyr Arg Thr Asn Trp Gly Tyr
        355                 360                 365
Trp Asn Leu Asn Pro Lys Gln Phe Met Thr Met Phe Pro His Thr Pro
370                 375                 380
Asp Asn Ser Phe Met Gly Phe Val Ser Glu Glu Leu Asn Glu Thr Glu
385                 390                 395                 400
Lys Arg Leu Ile Lys Gly Gly Lys Ala Ser Asn Met Ala Val Val Tyr
                405                 410                 415
Gly Lys Glu Ala Ser Ile Trp Lys Gly Lys Glu Lys Phe Leu Gly Ile
            420                 425                 430
Leu Asn Lys Tyr Met Glu Ile His Gly Thr Val Tyr Tyr Glu Ser Gln
        435                 440                 445
Arg Pro Pro Glu Val Pro Ala Phe Val Lys Asn His Gly Leu Leu Pro
450                 455                 460
Gln Pro Glu Phe Gln Gln Leu Leu Arg Lys Ala Lys Leu Phe Ile Gly
465                 470                 475                 480
Phe Gly Phe Pro Tyr Glu Gly Pro Ala Pro Leu Glu Ala Ile Ala Asn
                485                 490                 495
Gly Cys Ile Phe Leu Gln Ser Arg Phe Ser Pro Pro His Ser Ser Leu
            500                 505                 510
Asn His Glu Phe Phe Arg Gly Lys Pro Thr Ser Arg Glu Val Phe Ser
        515                 520                 525
Gln His Pro Tyr Ala Glu Asn Phe Ile Gly Lys Pro His Val Trp Thr
530                 535                 540
Val Asp Tyr Asn Asn Ser Glu Glu Phe Glu Ala Ala Ile Lys Ala Ile
545                 550                 555                 560
Met Arg Thr Gln Val Asp Pro Tyr Leu Pro Tyr Glu Tyr Thr Cys Glu
                565                 570                 575
Gly Met Leu Glu Arg Ile His Ala Tyr Ile Gln His Gln Asp Phe Cys
            580                 585                 590
Arg Ala Pro Asp Pro Ala Leu Pro Glu Ala His Ala Pro Gln Ser Pro
        595                 600                 605
Phe Val Leu Ala Pro Asn Ala Thr His Leu Glu Trp Ala Arg Asn Thr
610                 615                 620
Ser Leu Ala Pro Gly Ala Trp Pro Pro Ala His Ala Leu Arg Ala Trp
625                 630                 635                 640
Leu Ala Val Pro Gly Arg Ala Cys Thr Asp Thr Cys Leu Asp His Gly
                645                 650                 655
Leu Ile Cys Glu Pro Ser Phe Phe Pro Phe Leu Asn Ser Gln Asp Ala
            660                 665                 670
Phe Leu Lys Leu Gln Val Pro Cys Asp Ser Thr Glu Ser Glu Met Asn
        675                 680                 685
His Leu Tyr Pro Ala Phe Ala Gln Pro Gly Gln Glu Cys Tyr Leu Gln
690                 695                 700
Lys Glu Pro Leu Leu Phe Ser Cys Ala Gly Ser Asn Thr Lys Tyr Arg
```

```
                705                 710                 715                 720
Arg Leu Cys Pro Cys Arg Asp Phe Arg Lys Gly Gln Val Ala Leu Cys
                    725                 730                 735

Gln Gly Cys Leu
            740

<210> SEQ ID NO 4
<211> LENGTH: 790
<212> TYPE: PRT
<213> ORGANISM: Homo sapiens

<400> SEQUENCE: 4

Met Ile Thr Val Asn Pro Asp Gly Lys Ile Met Val Arg Arg Cys Leu
1               5                   10                  15

Val Thr Leu Arg Pro Phe Arg Leu Phe Val Leu Gly Ile Gly Phe Phe
                20                  25                  30

Thr Leu Cys Phe Leu Met Thr Ser Leu Gly Gly Gln Phe Ser Ala Arg
            35                  40                  45

Arg Leu Gly Asp Ser Pro Phe Thr Ile Arg Thr Glu Val Met Gly Gly
        50                  55                  60

Pro Glu Ser Arg Gly Val Leu Arg Lys Met Ser Asp Leu Leu Glu Leu
65                  70                  75                  80

Met Val Lys Arg Met Asp Ala Leu Ala Arg Leu Glu Asn Ser Ser Glu
                85                  90                  95

Leu His Arg Ala Gly Gly Asp Leu His Phe Pro Ala Asp Arg Met Pro
            100                 105                 110

Pro Gly Ala Gly Leu Met Glu Arg Ile Gln Ala Ile Ala Gln Asn Val
        115                 120                 125

Ser Asp Ile Ala Val Lys Val Asp Gln Ile Leu Arg His Ser Leu Leu
130                 135                 140

Leu His Ser Lys Val Ser Glu Gly Arg Arg Asp Gln Cys Glu Ala Pro
145                 150                 155                 160

Ser Asp Pro Lys Phe Pro Asp Cys Ser Gly Lys Val Glu Trp Met Arg
                165                 170                 175

Ala Arg Trp Thr Ser Asp Pro Cys Tyr Ala Phe Phe Gly Val Asp Gly
            180                 185                 190

Thr Glu Cys Ser Phe Leu Ile Tyr Leu Ser Glu Val Glu Trp Phe Cys
        195                 200                 205

Pro Pro Leu Pro Trp Arg Asn Gln Thr Ala Ala Gln Arg Ala Pro Lys
210                 215                 220

Pro Leu Pro Lys Val Gln Ala Val Phe Arg Ser Asn Leu Ser His Leu
225                 230                 235                 240

Leu Asp Leu Met Gly Ser Gly Lys Glu Ser Leu Ile Phe Met Lys Lys
                245                 250                 255

Arg Thr Lys Arg Leu Thr Ala Gln Trp Ala Leu Ala Ala Gln Arg Leu
            260                 265                 270

Ala Gln Lys Leu Gly Ala Thr Gln Arg Asp Gln Lys Gln Ile Leu Val
        275                 280                 285

His Ile Gly Phe Leu Thr Glu Glu Ser Gly Asp Val Phe Ser Pro Arg
290                 295                 300

Val Leu Lys Gly Gly Pro Leu Gly Glu Met Val Gln Trp Ala Asp Ile
305                 310                 315                 320

Leu Thr Ala Leu Tyr Val Leu Gly His Gly Leu Arg Val Thr Val Ser
                325                 330                 335
```

-continued

```
Leu Lys Glu Leu Gln Ser Asn Leu Gly Val Pro Pro Gly Arg Gly Ser
            340                 345                 350
Cys Pro Leu Thr Met Pro Leu Pro Phe Asp Leu Ile Tyr Thr Asp Tyr
            355                 360                 365
His Gly Leu Gln Gln Met Lys Arg His Met Gly Leu Ser Phe Lys Lys
        370                 375                 380
Tyr Arg Cys Arg Ile Arg Val Ile Asp Thr Phe Gly Thr Glu Pro Ala
385                 390                 395                 400
Tyr Asn His Glu Glu Tyr Ala Thr Leu His Gly Tyr Arg Thr Asn Trp
                405                 410                 415
Gly Tyr Trp Asn Leu Asn Pro Lys Gln Phe Met Thr Met Phe Pro His
            420                 425                 430
Thr Pro Asp Asn Ser Phe Met Gly Phe Val Ser Glu Glu Leu Asn Glu
            435                 440                 445
Thr Glu Lys Arg Leu Ile Lys Gly Gly Lys Ala Ser Asn Met Ala Val
            450                 455                 460
Val Tyr Gly Lys Glu Ala Ser Ile Trp Lys Gly Lys Glu Lys Phe Leu
465                 470                 475                 480
Gly Ile Leu Asn Lys Tyr Met Glu Ile His Gly Thr Val Tyr Tyr Glu
                485                 490                 495
Ser Gln Arg Pro Pro Glu Val Pro Ala Phe Val Lys Asn His Gly Leu
            500                 505                 510
Leu Pro Gln Pro Glu Phe Gln Leu Leu Arg Lys Ala Lys Leu Phe
            515                 520                 525
Ile Gly Phe Gly Phe Pro Tyr Glu Gly Pro Ala Pro Leu Glu Ala Ile
        530                 535                 540
Ala Asn Gly Cys Ile Phe Leu Gln Ser Arg Phe Ser Pro Pro His Ser
545                 550                 555                 560
Ser Leu Asn His Glu Phe Phe Arg Gly Lys Pro Thr Ser Arg Glu Val
                565                 570                 575
Phe Ser Gln His Pro Tyr Ala Glu Asn Phe Ile Gly Lys Pro His Val
            580                 585                 590
Trp Thr Val Asp Tyr Asn Asn Ser Glu Glu Phe Glu Ala Ala Ile Lys
            595                 600                 605
Ala Ile Met Arg Thr Gln Val Asp Pro Tyr Leu Pro Tyr Glu Tyr Thr
        610                 615                 620
Cys Glu Gly Met Leu Glu Arg Ile His Ala Tyr Ile Gln His Gln Asp
625                 630                 635                 640
Phe Cys Arg Ala Pro Asp Pro Ala Leu Pro Glu Ala His Ala Pro Gln
                645                 650                 655
Ser Pro Phe Val Leu Ala Pro Asn Ala Thr His Leu Glu Trp Ala Arg
            660                 665                 670
Asn Thr Ser Leu Ala Pro Gly Ala Trp Pro Ala His Ala Leu Arg
            675                 680                 685
Ala Trp Leu Ala Val Pro Gly Arg Ala Cys Thr Asp Thr Cys Leu Asp
        690                 695                 700
His Gly Leu Ile Cys Glu Pro Ser Phe Phe Pro Phe Leu Asn Ser Gln
705                 710                 715                 720
Asp Ala Phe Leu Lys Leu Gln Val Pro Cys Asp Ser Thr Glu Ser Glu
                725                 730                 735
Met Asn His Leu Tyr Pro Ala Phe Ala Gln Pro Gly Gln Glu Cys Tyr
            740                 745                 750
Leu Gln Lys Glu Pro Leu Leu Phe Ser Cys Ala Gly Ser Asn Thr Lys
```

```
              755                 760                 765
Tyr Arg Arg Leu Cys Pro Cys Arg Asp Phe Arg Lys Gly Gln Val Ala
        770                 775                 780

Leu Cys Gln Gly Cys Leu
785                 790

<210> SEQ ID NO 5
<211> LENGTH: 15
<212> TYPE: PRT
<213> ORGANISM: Artificial
<220> FEATURE:
<223> OTHER INFORMATION: preprotrypsin

<400> SEQUENCE: 5

Met Ser Ala Leu Leu Ile Leu Ala Leu Val Gly Ala Ala Val Ala
1               5                   10                  15

<210> SEQ ID NO 6
<211> LENGTH: 8
<212> TYPE: PRT
<213> ORGANISM: Artificial
<220> FEATURE:
<223> OTHER INFORMATION: FLAG-tag

<400> SEQUENCE: 6

Asp Tyr Lys Asp Asp Asp Asp Lys
1               5

<210> SEQ ID NO 7
<211> LENGTH: 1005
<212> TYPE: DNA
<213> ORGANISM: Homo sapiens

<400> SEQUENCE: 7
gagcagccac cggcgatccc cgaggccctg gcctggccca ctccacccac ccgcccagcc      60
ccggccccgt gccatgccaa cacctctatg gtcacccacc cggacttcgc cacgcagccg     120
cagcacgttc agaacttcct cctgtacaga cactgccgcc actttcccct gctgcaggac     180
gtgccccct ctaagtgcgc gcagccggtc ttcctgctgc tggtgatcaa gtcctcccct      240
agcaactatg tgcgccgcga gctgctgcgg cgcacgtggg gccgcgagcg caaggtacgg     300
ggtttgcagc tgcgcctcct cttcctggtg ggcacagcct ccaacccgca cgaggcccgc     360
aaggtcaacc ggctgctgga gctggaggca cagactcacg agacatcct gcagtgggac      420
ttccacgact ccttcttcaa cctcacgctc aagcaggtcc tgttcttaca gtggcaggag     480
acaaggtgcg ccaacgccag cttcgtgctc aacggggatg atgacgtctt tgcacacaca     540
gacaacatgg tcttctacct gcaggaccat gaccctggcc gccacctctt cgtgggcaa      600
ctgatccaaa acgtgggccc catccgggct ttttggagca agtactatgt gccagaggtg     660
gtgactcaga tgagcggta cccaccctat tgtgggggtg gtggcttctt gctgtcccgc      720
ttcacggccg ctgccctgcg ccgtgctgcc catgtcttgg acatcttccc cattgatgat     780
gtcttcctgg gtatgtgtct ggagcttgag ggactgaagc tgcctcccca gcggcatc      840
cgcacgtctg gcgtgcgggc tccatcgcaa cacctgtcct cctttgaccc ctgcttctac     900
cgagacctgc tgctggtgca ccgcttccta ccttatgaga tgctgctcat gtgggatgcg     960
ctgaaccagc ccaacctcac ctgcggcaat cagacacaga tctac                   1005

<210> SEQ ID NO 8
<211> LENGTH: 20
```

```
<212> TYPE: DNA
<213> ORGANISM: Artificial
<220> FEATURE:
<223> OTHER INFORMATION: primer

<400> SEQUENCE: 8
taggaattcc gagcagccac                                                 20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
cgcggatcct cagtagatct                                                 20
```

ANTIBODY FOR DETECTING EPITHELIAL OVARIAN CANCER MARKER AND METHOD FOR DIAGNOSING EPITHELIAL OVARIAN CANCER

CROSS-REFERENCE TO RELATED APPLICATIONS

This application is a national stage application under 35 U.S.C. §371 of PCT/JP2012/068980, filed Jul. 26, 2012, which claims benefit of Japanese Appl. No. 2011-163299, filed Jul. 26, 2011, which is incorporated herein by reference.

SEQUENCE LISTING

The Sequence Listing associated with this application is filed in electronic format via EFS-Web and hereby is incorporated by reference into the specification. The name of the text file containing the Sequence Listing is 14234783_Repl_Seq_List_ST25.txt. The size of the text file is 22 KB, and the text file was created on Mar. 10, 2014.

TECHNICAL FIELD

The present invention relates to an anti-β1,3-N-acetylglucosaminyltransferase 3 antibody for detection of an epithelial ovarian cancer marker, a hybridoma producing the antibody, and a method for diagnosis of epithelial ovarian cancer using the antibody.

BACKGROUND ART

Ovarian cancer is a cancer with a low incidence, compared with breast cancer or uterine cancer, among gynecologic cancers. Both incidence and mortality of this cancer, however, have been on the increase in recent years. In general, ovarian cancer is substantially asymptomatic early in the course of the disease and often found at the already advanced stage of symptoms. Hence, this disease has poor prognosis and exhibits the highest mortality among gynecologic cancers. Ovarian cancer is known to include, for example, surface epithelial-stromal tumors (hereinafter, referred to as "epithelial ovarian cancer") developed from surface epithelial cells in the ovary and germ cell tumors developed from germ cells, depending on the area affected. Of them, epithelial ovarian cancer accounts for approximately 90% of all ovarian cancer cases and is often seen particularly in middle-aged women in their 40s or older. Thus, the early detection of epithelial ovarian cancer is important for the treatment of the disease.

The ovary is an organ that has no contact with the outside of the body. Unlike the uterus, the ovary can be neither examined endoscopically nor subjected to cell harvest without abdominal section or perforation. In addition, epithelial ovarian cancer is generally difficult to detect by palpation before the ovary is enlarged at the advanced stage of symptoms. Hence, epithelial ovarian cancer is often undetected in ordinary examination or diagnosis methods. Although echography, MRI, CT, or the like is relatively effective for the early detection of epithelial ovarian cancer, this examination itself is extensive work with a high cost. In addition, these approaches, unfortunately, do not always have high diagnostic accuracy to distinguish between benign and malignant tumors.

Against this backdrop, tumor markers have received attention in recent years. The tumor markers refer to substances that are produced by cancer cells or produced by cells surrounding cancer cells in response to the cancer cells. The abundance of each tumor marker in a body fluid can reflect the presence or absence of tumor or the prognosis thereof and therefore serve as an index for, for example, cancer diagnosis and decision on therapeutic strategies. Also, this approach permits examination using a body fluid and is thus relatively low invasive. Advantageously, this examination is also convenient and low in cost.

Tumor markers composed of proteins such as CA125, CA602, CA130, CA72-4, CA546, CA19-9, and STN have been known so far as tumor markers for epithelial ovarian cancer (Non Patent Literatures 1 to 6). Methods for diagnosis of cancer using these tumor markers typically involve measuring the concentrations of the tumor markers in the serum of normal individuals and epithelial ovarian cancer patients and determining the presence or absence of cancer developed in a test subject on the basis of the difference in the levels.

These proteins, however, present specificity problems in such a way that CA125 exhibits positivity to a non-cancer benign gynecologic disease such as endometriosis or CA72-4, CA19-9, and STN exhibit positivity to various cancers of the digestive system including the stomach and the large intestine in addition to ovarian cancer. Epithelial ovarian cancer is further classified into serous, clear cell, mucinous, and endometrioid tumors depending on the histological type. The markers differ in reactivity among these histological types and therefore, do not correctly reflect the progression of cancer in some cases. For example, the ovarian cancer markers such as CA125, CA602, and CA546 have a low positive rate for mucinous ovarian cancer. Unfortunately, this histological type is therefore rarely detected even at the advanced stage.

Patent Literature 1 discloses a monoclonal antibody for use in the diagnosis of cancers including ovarian cancer against human galactosyltransferase associated with tumor (GAT) as a tumor marker, a hybridoma producing the antibody, and a method for assaying human galactosyltransferase associated with tumor in a specimen using the antibody. Also, Patent Literature 2 discloses a method for detecting gynecologic cancers early using glycosyltransferases β1,3-galactosyltransferase 5, β1,3-galactosyltransferase 4, and N-acetylglucosamine-6-O-sulfotransferase 2 as tumor markers. These glycosyltransferases used as tumor markers in Patent Literatures 1 and 2 are enzymes that synthesize sugar chains to be bound with, for example, glycoproteins, glycolipids or proteoglycans, and are usually anchored on Golgi membranes as membrane proteins localized to the Golgi bodies. Thus, these enzymes are not secreted to the outside of the cells and are therefore rarely detected in the body fluids of normal individuals. In ovarian cancer, however, it is known that glycosyltransferases are abnormally cleaved due to the increased expression level of a certain kind of protease and released to the outside of the cells. As a result, significant amounts of glycosyltransferase fragments are detected in body fluids.

The glycosyltransferase β1,4-galactosyltransferase described in Patent Literature 1 has an exceedingly high expression level among glycosyltransferases and is thus secreted in large amounts to the outside of the cell. Hence, this glycosyltransferase exhibits a serum concentration of approximately 200 ng/mL even in normal individuals and thus fails to distinguish between benign disease and cancer by its enzymatic activity alone. Accordingly, Patent Literature 1 was focused on the presence of a fragment of the abnormally cleaved glycosyltransferase in the culture supernatant of ovarian cancer cells and the ascitic fluid of an ovarian cancer patient. An antibody that recognizes only this fragment was used to attempt the construction of an assay system highly specific for ovarian cancer. Nonetheless, a commercially available clinical diagnosis kit based on this assay system exhibited positivity even for healthy women in some cases (Non Patent Literature 7). For this reason, GAT is currently used mainly in the monitoring of ovarian cancer recurrence and rarely used as a marker for early detection.

In Patent Literature 2, an attempt was made to detect marker candidate proteins in the blood of gynecologic cancer patients on the basis of reports stating that the expression of various proteins including glycosyltransferases is generally increased or decreased in cancer tissues. As a result, two glycosyltransferases were found to be useful in assay. The literature discloses an assay method according to the findings. In this case, however, the expression or synthesis products of these glycosyltransferases are reportedly related to digestive system cancers rather than gynecologic cancers. Although their expression was then confirmed in ovarian cancer cell lines (Non Patent Literature 8), there has been no report on the comparison of the expression levels between ovarian cancer or other gynecologic cancers and digestive system cancers.

As mentioned above, Patent Literatures 1 and 2 are directed only to the detection of markers in the body fluids of ovarian cancer patients with little consideration given to glycosyltransferase expression in ovarian cancer and disclose a glycosyltransferase fragment that happened to be measurable, as an ovarian cancer marker. This may lead to specificity problems as ovarian cancer markers.

CITATION LIST

Patent Literature

Patent Literature 1: JP Patent Publication (Kokai) No. 3-259093 A (1991)
Patent Literature 2: WO2009/028417

Non Patent Literature

Non Patent Literature 1: Bast R. C. Jr. et al., 1983, N. Engl. J. Med., 309: 883-887
Non Patent Literature 2: Suzuki M. et al., 1990, Nippon Gan Chiryo Gakkai Shi, 25: 1454-1460
Non Patent Literature 3: Inaba N. et al., 1989, Nippon Gan Chiryo Gakkai Shi, 24: 2426-2435
Non Patent Literature 4: Ohuchi N. et al., 1988, Gan To Kagaku Ryoho, 15, 2767-2772
Non Patent Literature 5: Nozawa S. et al., 1996, Nippon Rinsho, 54: 1665-1673
Non Patent Literature 6: Charpin C. et al., 1982, Int. J. Gynecol. Pathol., 1: 231-245
Non Patent Literature 7: Konica Minolta, Inc., GAT Test Kit product document
Non Patent Literature 8: Seko A. et al., 2009, Tumor Biol., 30: 43-50

SUMMARY OF INVENTION

Technical Problem

An object of the present invention is to provide an antibody or a fragment of the antibody capable of specifically recognizing and quantitatively and/or qualitatively detecting a tumor marker highly specific for epithelial ovarian cancer.

Another object of the present invention is to provide a method for conveniently and relatively low invasively diagnosis with high accuracy rate whether or not a test subject has epithelial ovarian cancer by quantitatively and/or qualitatively detecting an epithelial ovarian cancer marker using the antibody or the fragment thereof.

Solution to Problem

The present inventors have conducted diligent studies and consequently found that a glycosyltransferase β1,3-N-acetylglucosaminyltransferase 3 (hereinafter, the enzyme is also abbreviated to "B3GNT3" in the present specification) is present in larger amounts in the samples of epithelial ovarian cancer patients compared with normal individuals. The present invention is based on the findings and provides the following:

(1) An antibody for detection of an epithelial ovarian cancer marker recognizing, as an epitope, a part of a polypeptide consisting of the amino acid sequence represented by SEQ ID NO: 1.

(2) The antibody according to (1), wherein the antibody is a monoclonal antibody.

(3) The antibody according to (2), wherein the antibody is produced by a hybridoma identified by International Accession No. FERM BP-11494, or FERM BP-11495.

(4) A recombinant anti-B3GNT3 antibody for detection of an epithelial ovarian cancer marker comprising at least one set of corresponding light chain complementarity determining regions and heavy chain complementarity determining regions in an antibody according to any of (1) to (3).

(5) An antibody fragment for detection of an epithelial ovarian cancer marker, which is a fragment of an antibody according to any of (1) to (3) or a recombinant antibody according to (4) and having the activity of specifically recognizing B3GNT3.

(6) A hybridoma producing an antibody according to (2).

(7) The hybridoma according to (6), wherein the hybridoma is identified by International Accession No. FERM BP-11494.

(8) The hybridoma according to (6), wherein the hybridoma is identified by International Accession No. FERM BP-11495.

(9) A method for diagnosis of epithelial ovarian cancer, comprising quantitatively and/or qualitatively detecting a B3GNT3 polypeptide fragment present in a sample derived from a test subject, and determining the presence or absence of epithelial ovarian cancer developed in the test subject on the basis of the detection results.

(10) The method for diagnosis of epithelial ovarian cancer according to (9), wherein when the quantitative detection results of the B3GNT3 polypeptide fragment show a quantification value of the B3GNT3 polypeptide fragment equal to or higher than a predetermined value, the test subject is determined to be likely to have epithelial ovarian cancer.

(11) The method for diagnosis of epithelial ovarian cancer according to (9) or (10), wherein the B3GNT3 polypeptide fragment is the whole or a part of a polypeptide consisting of the amino acid sequence represented by SEQ ID NO: 1.

(12) The method for diagnosis of epithelial ovarian cancer according to any of (9) to (11), wherein the B3GNT3 polypeptide fragment is detected using at least one antibody, recombinant antibody, and/or antibody fragment selected from the group consisting of an antibody according to any of (1) to (3), a recombinant antibody according to (4), and an antibody fragment according to (5).

(13) The method for diagnosis of epithelial ovarian cancer according to (12), wherein two antibodies, recombinant antibodies, and/or antibody fragments that recognize different epitopes on the B3GNT3 polypeptide fragment are used.

(14) The method for diagnosis of epithelial ovarian cancer according to any of (9) to (13), further comprising quantitatively and/or qualitatively detecting a β1,6-N-acetylglucosaminyltransferase 5B (hereinafter, the enzyme is also abbreviated to "MGAT5B" in the present specification) polypeptide fragment present in the sample, and determining the presence or absence of epithelial ovarian cancer developed in the test subject on the basis of the detection results and the detection results according to any of (9) to (13).

(15) The method for diagnosis of epithelial ovarian cancer according to (14), wherein when the quantitative detection results of the MGAT5B polypeptide fragment show a quantification value of the MGAT5B polypeptide fragment equal to or higher than a predetermined value, the test subject is determined to be likely to have epithelial ovarian cancer.

(16) The method for diagnosis of epithelial ovarian cancer according to (14) or (15), wherein the MGAT5B polypeptide fragment is detected using at least one antibody, recombinant antibody, and/or antibody fragment selected from the group consisting of an anti-MGAT5B antibody recognizing, as an epitope, a part of a polypeptide consisting of the amino acid sequence represented by SEQ ID NO: 3, a recombinant anti-MGAT5B antibody comprising at least one set of corresponding light chain CDRs and heavy chain CDRs in the anti-MGAT5B antibody, and a fragment of the anti-MGAT5B antibody or the recombinant anti-MGAT5B antibody, the fragment having the activity of specifically recognizing MGAT5B.

(17) The method for diagnosis of epithelial ovarian cancer according to (16), wherein the anti-MGAT5B antibody is produced by a hybridoma identified by International Accession No. FERM BP-11496, FERM BP-11497, FERM BP-11498, or FERM BP-11499.

(18) The method for diagnosis of epithelial ovarian cancer according to any of (9) to (17), wherein the sample is a body fluid, a peritoneal lavage fluid, or a tissue.

The present specification encompasses the contents described in the specification and/or drawings of Japanese Patent Application No. 2011-163299 on which the priority of the present application is based.

Effects of Invention

The antibody of the present invention and/or the fragment thereof is capable of specifically recognizing and detecting a glycosyltransferase B3GNT3 polypeptide fragment as an epithelial ovarian cancer marker.

The hybridoma of the present invention can stably supply an anti-B3GNT3 monoclonal antibody capable of specifically recognizing and detecting a glycosyltransferase B3GNT3 as an epithelial ovarian cancer marker.

The method for diagnosis of epithelial ovarian cancer according to the present invention can detect epithelial ovarian cancer conveniently and relatively low invasively with high accuracy rate. As a result, whether or not a test subject has epithelial ovarian cancer can be determined early.

BRIEF DESCRIPTION OF DRAWINGS

FIG. 4a is a staining pattern of an epithelial ovarian cancer cell line RMUG-S immunostained with a GT117-2 antibody. FIG. 4b is a staining pattern of the cell line immunostained with a GT117-3 antibody. FIG. 4c is a staining pattern of the cell line immunostained with a positive control MAb8628 antibody.

DESCRIPTION OF EMBODIMENTS

Figure 1:
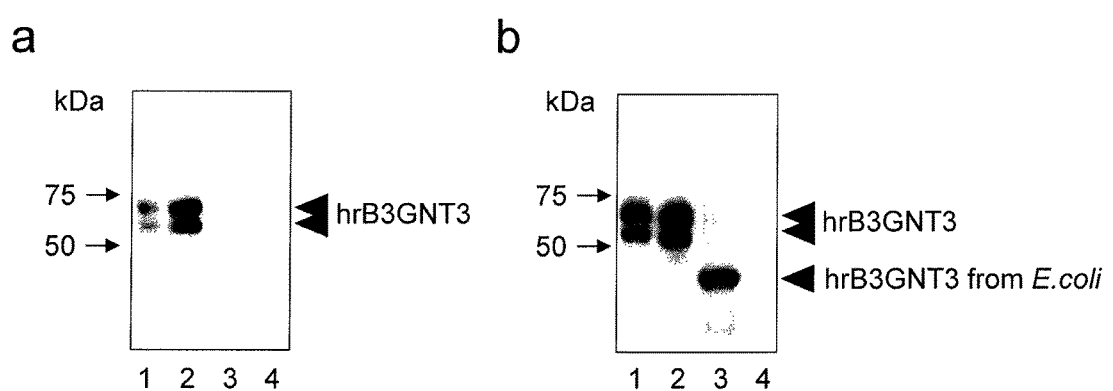
FIG. 1 shows results of Western blotting by which anti-B3GNT3 monoclonal antibodies (a: GT117-2 antibody and b: GT117-3 antibody) derived from hybridomas obtained in Example 1 were studied for their antigen specificity. Lane 1 shows the results about a FLAG-B3GNT3 polypeptide fragment. Lane 2 shows the results about a B3GNT3 polypeptide fragment from which the FLAG tag was cleaved off by enzymatic treatment. Lane 3 shows the results about a culture supernatant of E. coli allowed to express a B3GNT3 polypeptide fragment. Lane 4 shows the results about the normal human serum (NHS).

1. Antibody for Detection of Epithelial Ovarian Cancer Marker

1-1. Definition and Constitution

The first embodiment of the present invention relates to an antibody for detection of an epithelial ovarian cancer marker. The antibody of the present invention is an antibody that is used for detecting an epithelial ovarian cancer marker and recognizes and specifically binds to an epitope contained in the epithelial ovarian cancer marker.

In the present invention, the "epithelial ovarian cancer marker" refers to a biological marker for detection of epithelial ovarian cancer which is a biomaterial serving as an index showing that a test subject has epithelial ovarian cancer. The epithelial ovarian cancer marker according to the present invention is specifically a β1,3-N-acetylglucosaminyltransferase 3 polypeptide fragment.

"β1,3-N-acetylglucosaminyltransferase 3 (B3GNT3)" refers to one type of glycosyltransferase that is a membrane protein localized to the Golgi membrane and transfers N-acetylglucosamine with the β1-3 linkage. This enzyme has the function of elongating an O-linked sugar chain core 1 structure (Yeh J C. et al., 2001, Cell, 105: 957-969). B3GNT3 contains one N-terminal transmembrane domain and has an enzymatically active region as the C-terminal region. The B3GNT3 according to the present invention is the human-derived wild-type B3GNT3 composed of 372 amino acids and registered under GenBank Accession No. NP_055071.1. Specifically, the B3GNT3 according to the present invention is a polypeptide consisting of the amino acid sequence represented by SEQ ID NO: 2. Alternatively, the B3GNT3 according to the present invention may be human-derived wild-type B3GNT3 (GenBank Accession No. NP_055071.2) having Arg substituted for H is at residue 328 in SEQ ID NO: 2. In the present specification, B3GNT3 encompasses wild-type B3GNT3 and natural variants thereof.

In the present specification, the "natural variant" of B3GNT3 is a naturally occurring variant that contains the deletion, substitution, addition, or insertion of 1 to 10, preferably 1 to 5, more preferably 1 to 4, 1 to 3, or 1 or 2 amino acids in the amino acid sequence (SEQ ID NO: 2) constituting wild-type B3GNT3 or is a polypeptide exhibiting approximately 90% or higher, preferably approximately 95% or higher, more preferably approximately 98% or higher identity to the amino acid sequence represented by SEQ ID NO: 2. In this context, the "identity" refers to the ratio (%) of identical amino acid residues of a target amino acid sequence to the total number of amino acid residues of the amino acid sequence represented by SEQ ID NO: 2 including the number of gaps when the amino acid sequence represented by SEQ ID NO: 2 and the target amino acid sequence are aligned such that the maximum degree of identity can be achieved with or without introduced gaps. This identity can be determined using a protein search system based on BLASTP or FASTA. Specific examples of the natural variant include variants based on polymorphisms such as SNP (single-nucleotide polymorphism) and splicing variants. In this context, the natural variant of B3GNT3 is not necessarily required to have enzymatic activity equivalent to that of wild-type B3GNT3. This is because, reportedly, some natural variants of glycosyltransferases substantially lose activity even due to the substitution of only one amino acid (Nishihara S. et al., 1993, Biochem. Biophys. Res. Commun. 196: 624-631).

In the present specification, the "B3GNT3 polypeptide fragment" refers to a B3GNT3-derived polypeptide fragment that is released to the outside of the epithelial ovarian cancer cell as a result of abnormal cleavage by protease from the Golgi membrane in the cell and is capable of functioning as an epithelial ovarian cancer marker as mentioned above. Specifically, the B3GNT3 polypeptide fragment and a fragment derived from the polypeptide correspond to a polypeptide consisting of the whole or a part of the intra-Golgi C-terminal region of B3GNT3 except for the N-terminal region containing the transmembrane domain, for example, a polypeptide consisting of the whole or a part of an amino acid sequence (SEQ ID NO: 1) from glutamic acid at residue 38 (counted with initiating methionine as the 1st position) to downstream residues in human B3GNT3 shown in SEQ ID NO: 2.

The "antibody for detection of epithelial ovarian cancer" of the present invention refers to an antibody that is induced with the epithelial ovarian cancer marker B3GNT3 polypeptide fragment as an antigen. Thus, in the present specification, the "antibody for detection of an epithelial ovarian cancer marker" is also referred to as an "anti-B3GNT3 antibody". The anti-B3GNT3 antibody is capable of recognizing and binding to a part of the epithelial ovarian cancer marker as an epitope and specifically detecting the epithelial ovarian cancer marker. Specifically, a part of an amino acid consisting of the amino acid sequence represented by SEQ ID NO: 1 is used as an epitope. In this context, the term "a part" refers to one or more regions each composed of 5 to 15, preferably 5 to 10, more preferably 6 to 10 consecutive amino acids.

The anti-B3GNT3 antibody of the present invention may be any of polyclonal and monoclonal antibodies. A monoclonal antibody is preferable for achieving more specific detection. Specific examples of the anti-B3GNT3 monoclonal antibody include anti-B3GNT3 antibodies produced by hybridomas identified by International Accession No. FERM BP-11494, or FERM BP-11495. These antibodies will be described in detail in the paragraph "(3) Preparation of anti-B3GNT3 monoclonal antibody".

The anti-B3GNT3 antibody of the present invention can be modified. In this context, the "modification" includes functional modification necessary for antigen-specific binding activation, such as glycosylation, and labeling necessary for antibody detection. Examples of the antibody labeling include labeling using fluorescent dyes (FITC, rhodamine, Texas Red, Cy3, and Cy5), fluorescent proteins (e.g., PE, APC, and GFP), enzymes (e.g., horseradish peroxidase, alkaline phosphatase, and glucose oxidase), and biotin or (strept)avidin.

The modification on the anti-B3GNT3 antibody may be altered. For example, the glycosylation of the anti-B3GNT3 antibody may be altered in order to adjust the affinity of the anti-B3GNT3 antibody for the target antigen epithelial ovarian cancer marker. Specifically, examples thereof include alteration by which the glycosylation site in each framework region (FR) of the anti-B3GNT3 antibody is removed by the introduction of substitution into amino acid residue(s) constituting the glycosylation site to thereby delete glycosylation at the site.

Desirably, the anti-B3GNT3 antibody of the present invention has affinity for the epithelial ovarian cancer marker as high as a dissociation constant of $10^{-8}$ M or lower, preferably $10^{-9}$ M or lower, more preferably $10^{-10}$ M or lower. The dissociation constant can be measured using a technique known in the art. The dissociation constant may be measured using, for example, rate evaluation kit software of BIAcore system (GE Healthcare Japan Corp.).

The anti-B3GNT3 antibody of the present invention is not particularly limited by a globulin type and can be any of IgG, IgM, IgA, IgE, IgD, and IgY. IgG and IgM are preferred. Further, the anti-B3GNT3 antibody of the present invention is not particularly limited by an organism species of origin. The anti-B3GNT3 antibody of the present invention can be derived from every animal source including bird and mammals. Examples of such animal sources include mice, rats, guinea pigs, rabbits, goats, donkeys, sheep, camels, horses, chickens, and humans.

The anti-B3GNT3 polyclonal antibody or the anti-B3GNT3 monoclonal antibody of the present invention can be obtained by a production method mentioned later. Alternatively, the anti-B3GNT3 monoclonal antibody may be prepared by a chemical synthesis method or a recombinant DNA technique on the basis of its amino acid sequence. The anti-B3GNT3 monoclonal antibody may also be obtained from a hybridoma as described above. Alternatively, an anti-B3GNT3 antibody commercially available from each manufacturer (e.g., Novus Biologicals, LLC) may be used.

1-2. Preparation of Anti-B3GNT3 Antibody

The anti-B3GNT3 antibody of the present invention, i.e., the anti-B3GNT3 polyclonal antibody or the anti-B3GNT3 monoclonal antibody, and the hybridoma producing the anti-B3GNT3 monoclonal antibody can be prepared by a method described below. However, the production method of the present invention is not limited to the method described below, and any other method known in the art can be used in the preparation of the antibody or the hybridoma.
(1) Preparation of Immunogen The epithelial ovarian cancer marker is prepared as an immunogen. In the present invention, the epithelial ovarian cancer marker that may be used as an immunogen is, for example, the whole or a part of a human B3GNT3 polypeptide fragment having the amino acid sequence represented by SEQ ID NO: 1, or the whole or a part of a variant polypeptide fragment thereof.

The B3GNT3 polypeptide fragment as an immunogen can be prepared using, for example, a chemical synthesis method or a DNA recombination technique.

In the case of preparing the fragment using the chemical synthesis method, an appropriate B3GNT3 polypeptide fragment for use as an immunogen can be chemically synthesized by an approach known in the art, for example, a solid-phase peptide synthesis method, on the basis of information about, for example, the amino acid sequence of SEQ ID NO: 1.

In the case of preparing the fragment using the DNA recombination technique, a B3GNT3-encoding cDNA (B3GNT3 cDNA) can be incorporated into an appropriate expression system and expressed to obtain the B3GNT3 polypeptide fragment. Hereinafter, the method for preparing the B3GNT3 polypeptide fragment will be described with reference to specific examples.
(Preparation of B3GNT3 cDNA)

The B3GNT3 cDNA can be prepared by a technique known in the art, for example, a cDNA cloning method. Specifically, a human cDNA library is first prepared. The human cDNA library can be prepared by: extracting total RNAs according to a routine method from, for example, human fibroblasts (neuroblastoma cell line SK-N-MC) expressing the B3GNT3 gene or the like; then recovering poly-A(+) RNAs by treatment with oligo dT cellulose columns; and performing RT-PCR with the recovered RNAs as templates. Alternatively, a commercially available human cDNA library may be used.

Subsequently, the B3GNT3 cDNA clone of interest is isolated from the human cDNA library. Specifically, the clone can be isolated by a screening method known in the art, for example, a hybridization screening method, an expression screening method, or an antibody screening method, using primers and/or a probe appropriately designed on the basis of the B3GNT3 gene sequence. The B3GNT3 gene sequence is registered under Accession No. NM_014256 in the GenBank database. The primers are designed so that a B3GNT3 gene region encoding the amino acid sequence represented by SEQ ID NO: 1 is incorporated in an amplification fragment. An appropriate restriction site for cloning after isolation or a tag sequence for protein purification (FLAG, HA, His, myc, GFP, etc.) may be introduced to the 5' end of the forward or reverse primer. Also, the probe is designed with care so that a nucleic acid sequence encoding the amino acid sequence represented by SEQ ID NO: 1 in the B3GNT3 gene is incorporated in an amplification region. The isolated B3GNT3 cDNA clone may be amplified, if necessary, by a nucleic acid amplification method such as PCR.

The details of the cDNA cloning technique are described in, for example, Sambrook, J. et al., (1989) Molecular Cloning: A Laboratory Manual Second Ed., Cold Spring Harbor Laboratory Press, Cold Spring Harbor, N.Y. The description thereof can therefore be referred to.
(Preparation of B3GNT3 Expression Vector)

Next, the B3GNT3 cDNA clone thus obtained is incorporated into an expression vector. Specifically, examples thereof include plasmid and viral expression vectors. An expression vector for *E. coli* (e.g., pET21α series, pGEX4T series, pUC118 series, pUC119 series, pUC18 series, and pUC19 series), a *Bacillus subtilis*-derived expression vector (e.g., pUB 110 series and pTP5 series), a yeast-derived expression vector (e.g., YEp13 series, YEp24 series, and YCp50 series), an expression vector for insect cells (e.g., baculovirus), or an expression vector for animal cells (e.g., pA1-11, pXT1, pRc/CMV, pRc/RSV, and pcDNAI/Neo) can be used as the expression vector according to an expression host. The expression vector can usually contain, for example, a promoter, a terminator, an enhancer, a polyadenylation signal, a replication origin, and a selection marker, as regulatory elements. Also, the expression vector used may have a multicloning site for cloning of the cDNA fragment of interest or a tag sequence at the 5' or 3' end of the cDNA fragment insertion site for expression as a fusion polypeptide with a labeling peptide (tag) that facilitates purification. The expression vector used may further have a sequence encoding a secretory signal sequence, at the 5' end of the insertion site. As a result, an expressed mature polypeptide can be extracellularly secreted. Such expression vectors or other expression systems are commercially available as useful products from each manufacturer (Takara Bio Inc., Daiichi Pure Chemicals Co., Ltd., Agilent Technologies, Inc., Merck KGaA, Qiagen N.V., Promega K.K., Roche Diagnostics K.K., Life Technologies Corp., GE Healthcare Japan Corp., etc.). These products may therefore be used. For the insertion of the B3GNT3 cDNA to the expression vector, the purified B3GNT3 cDNA can be cleaved with appropriate restriction enzymes and inserted to a corresponding appropriate restriction site in the expression vector to ligate the cDNA fragment with the vector. If necessary, the B3GNT3 cDNA may be subcloned using an appropriate plasmid or the like before the incorporation into the expression vector.

The details of the cDNA cloning technique are also described in, for example, Sambrook, J. et al., (1989) Molecular Cloning: A Laboratory Manual Second Ed., Cold Spring Harbor Laboratory Press, Cold Spring Harbor, N.Y. The description thereof can therefore be referred to.

(Expression of B3GNT3 Polypeptide Fragment in Host Cell)

Subsequently, the obtained B3GNT3 expression system (e.g., B3GNT3 expression vector) is transferred to host cells to express the B3GNT3 polypeptide fragment of interest serving as an immunogen.

The host cells used are not particularly limited as long as the host cells are adaptable to the expression vector used in the preparation of the B3GNT3 expression vector and can express B3GNT3. For example, *Escherichia coli* (*E. coli*) can be used for the expression vector for *E. coli* used. *Bacillus subtilis* can be used for the *Bacillus subtilis*-derived expression vector used. Yeast (e.g., budding yeast: *Saccharomyces cerevisiae* and fission yeast: *Schizosaccharomyces pombe*) can be used for the yeast-derived expression vector used. Insect cells (e.g., Sf cells) can be used for the expression vector for insect cells used. Mammalian cells (e.g., HEK293, HeLa, COS, CHO, and BHK) or the like can be used for the expression vector for animal cells used. Alternatively, a cell-free translation system may be used. The B3GNT3 expression vector can be transferred to the host cells according to a DNA transfer method known in the art for each host cell without particular limitation. Examples of the method for transferring the vector to bacteria include a heat shock method, a calcium ion method, and electroporation. All of these techniques are known in the art and described in various literatures including Sambrook, J. et al., (1989) Molecular Cloning: A Laboratory Manual Second Ed., Cold Spring Harbor Laboratory Press, Cold Spring Harbor, N.Y. For example, a Lipofectin method (PNAS (1989) Vol. 86, 6077), electroporation, a calcium phosphate method (Virology (1973) Vol. 52, 456-467), or DEAE-dextran method is preferably used as a method for transferring the B3GNT3 expression vector to animal cells. Alternatively, a commercially available nucleic acid transfer agent such as Lipofectamine 2000 (Life Technologies Corp.) may be used. Transformants for B3GNT3 expression can be obtained by these procedures.

When the obtained transformants for B3GNT3 expression are microbes such as *E. coli* or yeast, any of natural and synthetic media that contain a carbon source, a nitrogen source, an inorganic salt, or the like utilizable by the microbes and permit efficient culture of the transformants can be used as a culture medium. Examples of the culture medium for *E. coli* include an LB medium. The transformants can be usually cultured at 37° C. for 6 to 24 hours under aerobic conditions such as shake culture or aeration-stirring culture. Preferably, the pH is kept around neutral pH during the culture period. If necessary, the medium may be supplemented with an antibiotic such as ampicillin or tetracycline.

When the transformants for B3GNT3 expression are mammalian cells or the like, these transformants can be cultured in a medium suitable for each cell. The medium may or may not contain serum. A serum-free medium is more desirable for the culture.

When the B3GNT3 expression vector is, for example, a protein expression-inducible vector containing a repressor gene and an operator, etc., the transformants are required to induce the expression of the B3GNT3 polypeptide fragment by predetermined treatment. The method for inducing the expression differs depending on a protein expression control system contained in the vector and can therefore involve induction treatment suitable for the system. For example, the protein expression control system most generally used for the protein expression-inducible vector in bacterial hosts is a system composed of a lac repressor gene and a lac operator. This system can induce expression by IPTG (isopropyl-1-thio-β-D-galactoside) treatment. The transformants having the B3GNT3 expression vector containing this system can express the B3GNT3 of interest by the addition of IPTG in an appropriate amount (e.g., final concentration: 1 mM) into the medium.

(Recovery of B3GNT3 Polypeptide Fragment)

Next, the B3GNT3 polypeptide fragment produced in the host cells is recovered from the cells or the culture supernatant thereof. When the produced B3GNT3 polypeptide fragment is accumulated within the microbial bodies or the cells, the microbial bodies or the cells are disrupted to extract the protein. When the B3GNT3 polypeptide fragment is produced to the outside of the microbial bodies or the outside of the cells, the culture solution may be used directly or a supernatant may be used after removal of the microbial bodies or the cells by centrifugation or the like. Then, the B3GNT3 polypeptide fragment can be isolated and purified using a general protein purification method. The B3GNT3 polypeptide fragment expressed as a fusion peptide with a labeling peptide (tag) can be isolated and purified using, for example, affinity chromatography suitable for each labeling peptide. Alternatively, the B3GNT3 polypeptide fragment expressed without the labeling peptide can be isolated and purified using, for example, an ammonium sulfate salting-out method, gel chromatography, ion-exchange chromatography, hydrophobic chromatography, or isoelectric focusing chromatography. Alternatively, two or more of these purification methods may be appropriately combined in the isolation and purification.

Finally, whether or not the B3GNT3 polypeptide fragment of interest has been successfully recovered can be confirmed by SDS-PAGE or the like. The recombinant B3GNT3 polypeptide fragment prepared by the above method retains glycosyltransferase activity and is soluble.

(2) Animal Immunization and Preparation of Anti-B3GNT3 Polyclonal Antibody

The obtained B3GNT3 polypeptide fragment can be used as an immunogen to obtain an anti-B3GNT3 polyclonal antibody that specifically recognizes the polypeptide.

First, the B3GNT3 polypeptide fragment is dissolved in a buffer solution to prepare an immunogen solution. If necessary, an adjuvant may be added thereto for efficient immunization. For example, a Freund's complete adjuvant (FCA), a Freund's incomplete adjuvant (FIA), an aluminum hydroxide gel, a *Bordetella pertussis* vaccine, Titer Max Gold (Vaxel, Inc.), or GERBU adjuvant (GERBU Biotechnik GmbH) can be used alone or as a mixture as the adjuvant.

Next, a mammal is immunized by the administration of the prepared immunogen solution. The animal used in the immunization is not particularly limited. For example, a non-human mammal, more specifically, a mouse, a rat, a hamster, a guinea pig, a rabbit, a goat, a donkey, a sheep, a camel, a horse, or the like can be used. Hereinafter, the immunization method according to the present invention will be described specifically by taking a mouse as an example.

Examples of the method for administering the immunogen solution include, but not limited to, subcutaneous injection using FIA or FCA, intraperitoneal injection using FIA, and intravenous injection using saline. Alternatively, the immunogen solution may be administered by intracutaneous injection or intramuscular injection. The single dose of the immunogen is appropriately determined according to the type of the animal to be immunized, an administration route, etc. In the case of a mouse, approximately 50 to 200 µg of the immunogen can be usually administered to a 4- to 10-week-old individual. The intervals between immunization shots are not particularly limited and are intervals of several days to several weeks, preferably 1 to 4 weeks. After the initial immunization, booster immunization is preferably performed. The number of booster shots is 2 to 6, preferably 3 to 4. After the initial immunization or later, blood is collected from the eye ground or the like of the immunized mouse, and an antibody titer in the serum is preferably measured by ELISA or the like. If a sufficient rise in the antibody titer can be confirmed, the immunogen solution can be intravenously or intraperitoneally injected to the mouse as the final immunization. Preferably, no adjuvant is used in the final immunization. Three to ten days, preferably 3 days, after the final immunization, blood is collected from the immunized mouse, and the serum can be treated according to a method known in the art (Antibodies: A Laboratory Manual, Cold Spring Harbor Laboratory, 1988) to obtain the anti-B3GNT3 polyclonal antibody.

(3) Preparation of Anti-B3GNT3 Monoclonal Antibody

The anti-B3GNT3 monoclonal antibody can be prepared according to the method of Kohler & Milstein (Nature 256: 495-497 (1975)). For example, hybridomas are prepared by the cell fusion between antibody-producing cells obtained from the immunized animal and myeloma cells. A clone producing the anti-B3GNT3 monoclonal antibody can be selected from the obtained hybridomas to prepare the monoclonal antibody of interest. Hereinafter, a specific example of the preparation will be described. However, the preparation of the antibody of the present invention is not limited to the method described below.

(Collection of Antibody-Producing Cell)

First, antibody-producing cells are collected from the immunized mouse. This collection is preferably performed 2 to 5 days after the final immunization day. Examples of the antibody-producing cells include spleen cells, lymph node cells, and peripheral blood cells. Spleen cells or local lymph node cells are preferred. The method for collecting the antibody-producing cells from the mouse can be performed according to a technique known in the art.

(Preparation of Hybridoma)

Subsequently, the antibody-producing cells can be fused with myeloma cells to prepare hybridomas producing the anti-B3GNT3 monoclonal antibody.

The myeloma cells used in the cell fusion are not particularly limited as long as the myeloma cells are of a generally available mouse-derived established cell line and can be proliferated in vitro. For convenient hybridoma screening in a step mentioned later, the myeloma cells preferably have drug selectivity and have the property of being unable to survive in an unfused state in a selective medium and being able to grow therein only in a state fused with the antibody-producing cells.

Various cell lines already known in the art are preferably used as the myeloma cells, for example, P3 (P3x63Ag8.653) (Kearney J. F. et al., 1979, J. Immunol., 123: 1548-1550), P3x63Ag8U.1 (Yelton D. E. et al., 1978, Curr. Top. Microbiol. Immunol., 81: 1-7), NS-1 (Kohler G. et al., 1976, Eur. J. Immunol., 6: 511-519), MPC-11 (Margulies D. H. et al., 1976, Cell, 8: 405-415), SP2/0 (Shulman M. et al., 1978, Nature, 276: 269-270), FO (de St. Groth S. F. et al., 1980, J. Immunol. Methods, 35: 1-21), 5194 (Trowbridge I. S. 1978, J. Exp. Med., 148: 313-323), or R210 (Galfre G. et al., 1979, Nature, 277: 131-133). These cell lines are available from RIKEN BioResource Center, ATCC (American Type Culture Collection), or ECACC (European Collection of Cell Cultures). These cell lines can be cultured and subcultured according to a culture method known in the art (e.g., Antibodies: A Laboratory Manual, Cold Spring Harbor Laboratory, 1988; and Selected Methods in Cellular Immunology, W.H. Freeman and Company, 1980). Examples of the selective medium include a HAT medium (RPMI1640 medium supplemented with 100 units/mL penicillin, 100 µg/mL streptomycin, 10% fetal bovine serum (FBS), $10^{-4}$ M hypoxanthine, $1.5 \times 10^{-5}$ M thymidine, and $4 \times 10^{-7}$ M aminopterin).

For the cell fusion between the myeloma cells and the antibody-producing cells, the obtained spleen cells and the myeloma cells are washed. Then, the myeloma cells and the antibody-producing cells can be mixed at a mixing ratio of 1:1 to 1:10 in a medium for animal cell culture such as a MEM, DMEM, or RPMI1640 medium or a commercially available medium for cloning or cell fusion (preferably, serum-free) and contacted with each other at 30 to 37° C. for 1 to 15 minutes in the presence of a cell fusion promoter. For example, polyethylene glycol (hereinafter, referred to as "PEG") having an average molecular weight of 1,500 to 4,000 Da can be used as the cell fusion promoter at a concentration of approximately 10 to 80%. Alternatively, a fusion promoter or a fusion virus such as polyvinyl alcohol or Sendai virus may be used. Usually, PEG having an average molecular weight of 1,500 Da is preferably used. If necessary, an aid such as dimethyl sulfoxide may be used in combination therewith in order to enhance fusion efficiency. Alternatively, the antibody-producing cells and the myeloma cells may be fused using a commercially available cell fusion apparatus based on electric stimulation (e.g., electroporation) (Nature, 1977, Vol. 266, 550-552).

After the cell fusion treatment, the cells are washed with the medium used in the myeloma cell fusion (e.g., RPMI1640 medium). Then, a cell suspension is prepared. Subsequently, the cell suspension is appropriately diluted with, for example, an RPMI1640 medium containing FBS and then added at a density of approximately $1 \times 10^4$ cells to a 96-well plate. The selective medium is added to each well where the cells can then be cultured with the selective medium appropriately replaced with a fresh one. The culture temperature is 20 to 40° C., preferably approximately 37° C. In the case of using an HGPRT-deficient or thymidine kinase (TK)-deficient line as the myeloma cells, only hybridomas of the antibody-producing cells and the myeloma cells can be selectively grown and proliferated by use of a selective medium containing hypoxanthine, aminopterin, and thymidine (HAT medium). Thus, cells grown from approximately 10 days after the start of the culture in the selective medium can be selected as hybridomas.

Next, the culture supernatants of the proliferated hybridomas are screened for a hybridoma containing the anti-B3GNT3 monoclonal antibody of interest. For the hybridoma screening, for example, a part of the culture supernatant contained in the well of each cultured hybridoma can be collected and screened by enzyme immunoassay (ELISA, etc.), radioimmunoassay (RIA), or the like with the binding activity against the B3GNT3 polypeptide fragment used as an immunogen as an index. The antibody-producing hybridomas are cloned in order to obtain a hybridoma further stably producing the monoclonal antibody. The cloning can be performed by a usual method such as a limiting dilution method or a fluorescence-activated cell sorter method without particular limitations. These screening and cloning methods can be combined to finally establish hybridomas as anti-B3GNT3 monoclonal antibody-producing cells.

If necessary, cross reactivity may be tested. Specifically, only a hybridoma producing an antibody that exhibits acceptable cross reactivity is selected by study on its binding activity against other proteins including other glycosyltransferases, etc. The acceptable cross reactivity means the non-specific binding activity of the monoclonal antibody at a negligible level for the use of interest.

Specific examples of the anti-B3GNT3 monoclonal antibody-producing hybridoma thus selected by the screening method include GT117-2 (National Deposition No: FERM P-22095; International Accession No: FERM BP-11494), or GT117-3 (National Deposition No: FERM P-22096; International Accession No: FERM BP-11495). These hybridomas were nationally deposited on Apr. 4, 2011 with International Patent Organism Depositary, National Institute of Advanced Industrial Science and Technology (Tsukuba Central 6, 1-1-1 Higashi, Tsukuba, Ibaraki, Japan) and internationally deposited on the same date with International Patent Organism Depositary, National Institute of Technology and Evaluation (Tsukuba Central 6, 1-1-1 Higashi, Tsukuba, Ibaraki, Japan (post code: 305-8566)).

These hybridoma cell lines can be preferably cultured at 37° C. using an RPMI1640 medium supplemented with 10% FBS.

(Recovery of Anti-B3GNT3 Monoclonal Antibody)

The anti-B3GNT3 monoclonal antibody can be recovered by a common technique. The anti-B3GNT3 monoclonal antibody can be recovered from the established hybridoma by the adoption of for example, a usual cell culture method or an ascites formation method. The cell culture method involves: culturing the anti-B3GNT3 monoclonal antibody-producing hybridoma in an animal cell culture medium such as an RPMI1640 medium containing 10% FBS, a MEM medium, or a serum-free medium, for example, at 37° C. for 2 to 10 days in a 5% $CO_2$ atmosphere; and obtaining the antibody from the culture supernatant thereof. The ascites formation method involves intraperitoneally administering the anti-B3GNT3 monoclonal antibody-producing hybridoma at a dose of approximately 10,000,000 cells to an animal of the same species (in the case of the above method, a mouse) as the mammal from which the myeloma cells are derived to proliferate the hybridoma in large amounts. One to two weeks later, the ascitic fluid or serum of the animal can be collected to recover the monoclonal antibody of interest. A "GT117-2 antibody", or a "GT117-3 antibody" can also be obtained by such a method from GT117-2, or GT117-3, respectively, listed above as specific examples of the anti-B3GNT3 monoclonal antibody-producing hybridoma.

The antibody can be purified, if necessary, using an appropriate purification method known in the art. The antibody can be purified using, for example, ion-exchange chromatography, affinity chromatography using protein A or protein G, gel chromatography, or an ammonium sulfate salting-out method.

1-3. Epithelial Ovarian Cancer Detection Reagent

The anti-B3GNT3 antibody of the present invention, a recombinant antibody for detection of an epithelial ovarian cancer marker, and/or an antibody fragment for detection of an epithelial ovarian cancer marker mentioned later specifically react with the epithelial ovarian cancer marker and as such, can be used as an active ingredient in an epithelial ovarian cancer detection reagent. This detection reagent can also be used to detect the epithelial ovarian cancer marker contained in a sample collected from a test subject, thereby diagnosing epithelial ovarian cancer developed in the test subject.

The detection reagent of the present invention can be used in any means using an immunological approach. The detection reagent of the present invention can be used in combination with, for example, a reagent for a fully automatic immunoassay apparatus (e.g., chemiluminescent enzyme immunoassay (CLEIA) apparatus) to diagnose epithelial ovarian cancer conveniently and rapidly. This will be described in detail in the fourth embodiment. Also, the epithelial ovarian cancer detection reagent can be used for staining of epithelial ovarian cancer tissues. For example, the presence or absence of the epithelial ovarian cancer marker in tissues obtained at laparotomy or by needlestick can be detected by immunostaining to determine the presence or absence of epithelial ovarian cancer developed in the subject. Alternatively, the presence or absence of the epithelial ovarian cancer marker can be detected by a method such as Western blotting using extracts of the collected tissues to determine the presence or absence of epithelial ovarian cancer developed in the subject.

1-4. Effect

The anti-B3GNT3 antibody of the present invention is capable of specifically recognizing and binding to the intra-Golgi region of the epithelial ovarian cancer marker glycosyltransferase B3GNT3. Thus, use of the anti-B3GNT3 antibody of the present invention achieves efficient detection of the epithelial ovarian cancer marker from a sample of a test subject.

2. Recombinant Antibody for Detection of Epithelial Ovarian Cancer Marker

2-1. Definition and Constitution

The second embodiment of the present invention relates to a recombinant antibody for detection of an epithelial ovarian cancer marker. The recombinant antibody of the present invention comprises at least one set of corresponding light chain complementarity determining regions (CDRs) and heavy chain CDRs in the antibody for detection of an epithelial ovarian cancer marker according to the first embodiment. In the present specification, the "recombinant antibody for detection of an epithelial ovarian cancer marker" is also referred to as a "recombinant anti-B3GNT3 antibody".

In the present specification, the "recombinant antibody" refers to, for example, a chimeric antibody, a humanized antibody, and a synthetic antibody.

The "chimeric antibody" refers to an antibody derived from a certain antibody by the replacement of its light chain and heavy chain constant regions (C regions) with light chain and heavy chain C regions of another antibody. The chimeric antibody corresponds to, for example, an antibody derived from the mouse anti-human B3GNT3 monoclonal antibody GT117-2 antibody, or GT117-3 antibody by the replacement of its light chain and heavy chain C regions with C regions of an appropriate human antibody. Specifically, the chimeric antibody has CDR-containing variable regions (V regions) derived from the GT117-2 antibody, or the GT117-3 antibody and C regions derived from the human antibody.

The "humanized antibody", also called reshaped human antibody, refers to a mosaic antibody derived from a non-human mammal antibody, for example, an anti-human B3GNT3 mouse antibody, by the replacement of only its light chain V region (VL) and heavy chain V region (VH) CDRs with CDRs of an appropriate human antibody. For example, DNA sequences encoding CDR regions (CDR1 to CDR3) derived from the GT117-2 antibody, or the GT117-3 antibody are replaced with DNA sequences encoding corresponding CDRs derived from the human antibody to prepare a recombinant antibody gene, which can then be expressed to obtain a recombinant antibody that mimics the properties of the particular antibody. A general gene recombination approach for preparing the humanized antibody is also known. Examples of such approaches include a method which involves: designing DNA sequences so that mouse antibody CDRs are linked to human antibody framework regions (FRs); and synthesizing the DNA sequences by PCR using a few oligonucleotide primers prepared to have a part overlapping with the terminal regions of both CDR- and FR-encoding sequences (European Patent Application Publication No. EP 125023).

The "synthetic antibody" refers to an antibody synthesized using a chemical method or a recombinant DNA method. The synthetic antibody corresponds to, for example, a monomeric polypeptide molecule comprising one or more VLs of a particular antibody and one or more VHs thereof artificially linked via a linker peptide or the like having an appropriate length and sequence, or a multimeric polypeptide thereof. Specific examples of such polypeptides include a single chain fragment of variable region (scFv) (see Pierce Catalog and Handbook, 1994-1995, Pierce Chemical Co., Rockford, Ill.), a diabody, a triabody, and a tetrabody. In an immunoglobulin molecule, VL and VH are typically located on separate polypeptide chains (light chain and heavy chain). The scFv refers to a synthetic antibody fragment having a structure in which the V regions on these two polypeptide chains are linked via a flexible linker having a sufficient length to form a single polypeptide chain. Both the V regions in the scFv can form one functional antigen-binding site by the self-assembly of these regions. The scFv can be obtained by a technique known in the art which involves integrating a recombinant DNA encoding the scFv into a phage genome and expressing the DNA. The diabody refers to a molecule having a structure based on the structure of a scFv dimer (Holliger et al., 1993, Proc. Natl. Acad. Sci. USA 90: 6444-6448). For example, when the linker is shorter than approximately 12 amino acid residues in length, two variable domains in the scFv cannot self-assemble. By contrast, the formation of the diabody, i.e., the interaction between two scFvs, can allow VL on one Fv chain to assemble with VH on the other Fv chain to form two functional antigen-binding sites (Marvin et al., 2005, Acta Pharmacol. Sin. 26: 649-658). Alternatively, cysteine residues may be added to the C termini of scFvs to form a stable diabody through the disulfide bond between these two Fv chains (Olafsen et al., 2004, Prot. Engr. Des. Sel. 17: 21-27). Although the diabody is such a divalent antibody fragment, its two antigen-binding sites do not have to bind to the same epitope and may be bispecific to respectively recognize and specifically bind to different epitopes. The triabody and the tetrabody have trimeric and tetrameric structures, respectively, based on the scFv structure, as with the diabody. The triabody and the tetrabody are trivalent and tetravalent antibody fragments, respectively, and may be multispecific antibodies.

2-2. Preparation of Recombinant Anti-B3GNT3 Antibody

The recombinant anti-B3GNT3 antibody can be prepared by a DNA cloning technique known in the art using the anti-B3GNT3 antibody prepared in the first embodiment. For example, each literature cited above as well as Sambrook, J. et al., (1989) Molecular Cloning: A Laboratory Manual Second Ed., Cold Spring Harbor Laboratory Press, Cold Spring Harbor, N.Y. can be referred to.

2-3. Effect

The recombinant anti-B3GNT3 antibody of the present invention is capable of specifically recognizing and binding to the intra-Golgi region of the epithelial ovarian cancer marker glycosyltransferase B3GNT3, as with the anti-B3GNT3 antibody of the first embodiment. Thus, use of the recombinant anti-B3GNT3 antibody of the present invention achieves efficient detection of the epithelial ovarian cancer marker from a sample of a test subject.

3. Antibody Fragment for Detection of Epithelial Ovarian Cancer Marker 3-1. Definition and Constitution The third embodiment of the present invention relates to an antibody fragment for detection of an epithelial ovarian cancer marker.

The "antibody fragment" of the present invention refers to a partial region of the anti-B3GNT3 antibody according to the first embodiment or the recombinant anti-B3GNT3 antibody according the second embodiment. This partial region is a polypeptide chain having activity substantially equivalent to the B3GNT3-specific recognition and binding activity of the antibody, or a complex of the polypeptide chain. Specifically, the antibody fragment corresponds to a partial antibody region containing at least one of the antigen-binding site(s) contained in the anti-B3GNT3 antibody of the first embodiment or the recombinant anti-B3GNT3 antibody of the second embodiment, i.e., a polypeptide chain having at least one set of VL and VH, or a complex thereof. Examples of the fragment of the anti-B3GNT3 antibody of the first embodiment include a large number of sufficiently characterized fragments formed by the cleavage of the antibody with various peptidases. Specific examples of the antibody fragment include Fab, F(ab')$_2$, and Fab'. The Fab refers to a fragment that is formed by the papain cleavage of an IgG molecule at a site N-terminal to the hinge disulfide bond and composed of a polypeptide consisting of VH and CH1 (VH-adjacent domain among three domains (CH1, CH2, and CH3) constituting the heavy chain constant region (H chain C region; hereinafter, referred to as "CH")) and a light chain. The F(ab')$_2$ refers to a Fab' dimer that is formed by the pepsin cleavage of an IgG molecule at a site C-terminal to the hinge disulfide bond. The Fab' has a structure substantially equivalent to that of Fab except that the H chain is slightly longer than that of Fab by containing the hinge region. The Fab' can be obtained by the reduction of F(ab')$_2$ under mild conditions and the subsequent cleavage of the disulfide bond in the hinge region. All of these antibody fragments contain an antigen-binding site and are therefore able to specifically bind to the antigen (i.e., B3GNT3 in the present invention).

3-2. Effect

The antibody fragment for detection of an epithelial ovarian cancer marker of the present invention is capable of specifically recognizing and binding to the intra-Golgi region of the epithelial ovarian cancer marker glycosyltransferase B3GNT3, as with the anti-B3GNT3 antibody of the first embodiment. Thus, use of the antibody fragment for detection of an epithelial ovarian cancer marker of the present invention achieves efficient detection of the epithelial ovarian cancer marker from a sample of a test subject.

4. Method for Diagnosis of Epithelial Ovarian Cancer

The fourth embodiment of the present invention relates to a method for diagnosis of epithelial ovarian cancer. The method for diagnosis of epithelial ovarian cancer according to the present invention comprises quantitatively and/or qualitatively detecting an epithelial ovarian cancer marker present in a sample derived from a test subject, and determining the presence or absence of epithelial ovarian cancer developed in the test subject on the basis of the detection results.

4-1. Definition and Constitution

In the present specification, the "test subject" refers to an individual to be subjected to examination in the method of the present invention, i.e., an individual who provides a sample mentioned later. The test subject is preferably an individual who may have epithelial ovarian cancer or an epithelial ovarian cancer patient. In the present specification, the "normal individual" refers to a normal individual in a broad sense who is normal in terms of epithelial ovarian cancer, i.e., an individual having no epithelial ovarian cancer. Thus, the normal individual may have other diseases, for example, gastric cancer or uterine cancer as long as the normal individual has no epithelial ovarian cancer. The normal individual is preferably a normal individual in a narrow sense who has no disease, i.e., a healthy individual.

The "sample" refers to a material that is collected from the test subject and directly subjected to the method of the present invention. The sample corresponds to, for example, a body fluid, a peritoneal lavage fluid, or a tissue. The "body fluid" refers to a biological sample in a liquid state collected directly from the test subject. Examples thereof include blood (including serum, plasma, and interstitial fluid), lymph, spinal fluid, ascitic fluid, pleural effusion, sputum, lacrimal fluid, nasal discharge, saliva, urine, vaginal fluid, and semen. The "tissue" includes sections and extracts. In the method of the present invention, the sample is preferably a body fluid such as blood, lymph, or ascitic fluid, or a peritoneal lavage fluid.

The sample can be collected according to a method known in the art. For example, blood or lymph can be obtained according to a blood collection method known in the art. Specifically, peripheral blood can be collected by injection to a peripheral vein or the like. Alternatively, ascitic fluid or the peritoneal lavage fluid can be collected by transabdominal ultrasound-guided aspiration steering around the intestinal tract or collected by aspiration using a syringe or the like from the Douglas' pouch after intraperitoneal injection of approximately 100 mL of saline during abdominal section. The tissue can be collected by direct needling to the organ or collected from a site resected during surgery. The sample thus collected from the test subject can be used, if necessary, after dilution or concentration or after pretreatment such as the addition of an anticoagulant such as heparin or fixation with a fixative such as paraffin (in the case of the tissue). Alternatively, the sample may be used directly without such pretreatment.

The sample may be used immediately after collection or may be used by treatment such as thawing, if necessary, after cryopreservation for a given period. In the method of the present invention, a volume of 10 μL to 100 μL usually suffices for epithelial ovarian cancer marker detection in the case of using serum or a peritoneal lavage fluid as the sample.

In the method of the present invention, the epithelial ovarian cancer marker to be detected is the B3GNT3 polypeptide fragment described in the first embodiment. Specifically, the epithelial ovarian cancer marker is a polypeptide fragment consisting of an amino acid sequence that is located in an intra-Golgi region and corresponds to the C-terminal region of B3GNT3. The epithelial ovarian cancer marker corresponds to, for example, the whole or a part of a polypeptide consisting of the amino acid sequence represented by SEQ ID NO: 1 in human B3GNT3.

4-2. Method for Detecting Epithelial Ovarian Cancer Marker

The method for detecting the epithelial ovarian cancer marker in the sample may be any method as long as the method used is known in the art and is capable of detecting the polypeptide marker. The method is preferably a detection method based on immunological reaction (immunological detection method) using an antibody that specifically recognizes and binds to the epithelial ovarian cancer marker.

The anti-B3GNT3 antibody according to the first embodiment (including the anti-B3GNT3 polyclonal antibody and the anti-B3GNT3 monoclonal antibody), the recombinant anti-B3GNT3 antibody according to the second embodiment, and/or the antibody fragment according to the third embodiment can be used as the epithelial ovarian cancer marker-specific antibody (hereinafter, referred to as an "anti-epithelial ovarian cancer marker antibody"). Specifically, examples thereof include the mouse anti-human B3GNT3 monoclonal antibodies GT117-2 antibody, or GT117-3 antibody described in the first embodiment.

Examples of the immunological detection method for detecting the amount of the epithelial ovarian cancer marker present in the test subject-derived sample include enzyme immunoassay (including ELISA and EIA), fluorescent immunoassay, radioimmunoassay (RIA), luminescent immunoassay, a surface plasmon resonance (SPR) method, a quartz crystal microbalance (QCM) method, immunoturbidimetry, latex agglutination immunoassay, latex turbidimetry, hemagglutination, a particle agglutination method, a gold colloid method, capillary electrophoresis, Western blotting, and an immunohistochemical method (immunostaining method). All of these methods are known in the art and can be performed according to usual methods in the art as a rule.

When the epithelial ovarian cancer marker of the present invention is assayed by the immunoassay using labeling such as enzyme immunoassay, fluorescent immunoassay, radioimmunoassay, or luminescent immunoassay, the immunological reaction is preferably performed after immobilization of the anti-epithelial ovarian cancer marker antibody or the like or after immobilization of a component (i.e., the epithelial ovarian cancer marker) in the sample.

An insoluble carrier having a shape such as beads, a microplate, a test tube, a stick, or a test piece made of a material such as polystyrene, polycarbonate, polyvinyltoluene, polypropylene, polyethylene, polyvinyl chloride, nylon, polymethacrylate, latex, gelatin, agarose, cellulose, Sepharose, glass, metal, ceramics, or magnetic materials can be used as a solid-phase carrier. The immobilization can be achieved by the binding of the anti-epithelial ovarian cancer marker antibody or the epithelial ovarian cancer marker to the solid-phase carrier according to a method known in the art such as a physical adsorption method, a chemical binding method, or combined use thereof.

Examples of the label used for labeling the anti-epithelial ovarian cancer marker antibody in enzyme immunoassay include peroxidase (POD), alkaline phosphatase, β-galactosidase, urease, catalase, glucose oxidase, lactate dehydrogenase, amylase, and biotin (or avidin). Examples of the label in fluorescent immunoassay include fluorescein isothiocyanate, tetramethylrhodamine isothiocyanate, substituted rhodamine isothiocyanate, dichlorotriazine isothiocyanate, Alexa, and Alexa Fluor. Examples of the label in radioimmunoassay include tritium, iodine 125, and iodine 131. In luminescent immunoassay, for example, NADH, FMNH2, a luciferase system, a luminol-hydrogen peroxide-POD system, an acridinium ester system, or a dioxetane compound system can be used as the label.

The labeling material can be bound to the antibody by a method known in the art such as a glutaraldehyde method, a maleimide method, a pyridyl disulfide method, or a periodic acid method for enzyme immunoassay or by a method known in the art such as a chloramine T method or a Bolton-Hunter method for radioimmunoassay. The assay procedures can be performed according to a method known in the art (Current protocols in Protein Sciences, 1995, John Wiley & Sons Inc.; and Current protocols in Immunology, 2001, John Wiley & Sons Inc.).

The immunoassay includes a direct detection method which involves labeling the anti-epithelial ovarian cancer marker antibody and quantifying the epithelial ovarian cancer marker in the sample by direct detection, and an indirect detection method which involves quantifying the epithelial ovarian cancer marker in the sample by indirect detection using a labeled secondary antibody. Either of the methods may be used in the present invention.

In the case of the direct detection method, for example, the polypeptide fragment in the sample is immobilized on the carrier and contacted with the labeled anti-epithelial ovarian cancer marker antibody to form a complex of the epithelial ovarian cancer marker of the present invention and the labeled anti-epithelial ovarian cancer marker antibody. Then, unbound labeled antibodies are washed off. From the amount of the bound labeled antibody or the amount of the unbound labeled antibody, the epithelial ovarian cancer marker in the sample can be detected and the amount thereof can be measured.

In the case of the indirect detection method, the epithelial ovarian cancer marker in the sample is reacted with the anti-epithelial ovarian cancer marker antibody as a primary antibody (primary reaction) and further reacted with a labeled secondary antibody (secondary reaction). The primary reaction and the secondary reaction may be performed in reverse order or may be performed simultaneously. The labeled secondary antibody may specifically recognize and bind to the primary antibody or may recognize and bind to the epithelial ovarian cancer marker. The primary reaction and the secondary reaction form a complex consisting of the immobilized epithelial ovarian cancer marker, the anti-epithelial ovarian cancer marker antibody, and the labeled secondary antibody or a complex consisting of the immobilized anti-epithelial ovarian cancer marker antibody, the epithelial ovarian cancer marker, and the labeled secondary antibody.

The indirect detection method involving forming the complex of the immobilized anti-epithelial ovarian cancer marker antibody, the epithelial ovarian cancer marker, and the labeled secondary antibody is called sandwich method. This method detects the antigen of interest using two different types of antibodies capable of concurrently binding to the same antigen, i.e., two or more types of monoclonal antibodies (or at least one type of polyclonal antibody) that recognize different epitopes on one antigen. So-called sandwich ELISA, which involves immobilizing one of these two types of antibodies onto the carrier, labeling the other antibody, and detecting the antigen of interest, is frequently used as the sandwich method. This method can also be preferably used in the method of the present invention. After the complex formation, proteins other than the epithelial ovarian cancer marker contained in the sample and unbound labeled secondary antibodies are washed off. From the amount of the bound labeled secondary antibody or the amount of the unbound labeled secondary antibody, the epithelial ovarian cancer marker in the sample can be detected and the amount thereof can be measured. The indirect detection method based on the sandwich method is preferably used because the epithelial ovarian cancer marker in the sample can be assayed highly precisely without sacrificing sensitivity. This approach is also applicable to automatization using an existing automatic immunological detection apparatus.

A preferred exemplary embodiment of the detection of the epithelial ovarian cancer marker of the present invention will be shown. First, the anti-epithelial ovarian cancer marker antibody of the present invention (e.g., either the GT117-2 antibody or the GT117-3 antibody) is immobilized as a primary antibody onto the insoluble carrier. After the immobilization, the antibody-nonimmobilized solid-phase surface is blocked with a protein irrelevant to the antigen epithelial ovarian cancer marker (e.g., fetal calf serum, bovine serum albumin, and gelatin) or a non-protein blocking agent such as sucrose or a chemically synthesized polymer. Next, the immobilized primary antibody is contacted with the test subject-derived sample. Subsequently, another anti-epithelial ovarian cancer marker antibody (in the above case, the other of the GT117-2 antibody, or the GT117-3 antibody) that recognizes and binds to an epitope different from that for the primary antibody on the epithelial ovarian cancer marker is contacted therewith as a secondary antibody. The secondary antibody used is a labeled secondary antibody obtained by the above labeling method. Then, unbound labeled secondary antibodies are removed by washing. Then, a signal derived from the label on the labeled secondary antibody bound with the carrier can be detected.

4-3. Diagnosis of Developed Epithelial Ovarian Cancer

Epithelial ovarian cancer developed in the test subject is diagnosed on the basis of detection results obtained by quantitatively and/or qualitatively detecting the epithelial ovarian cancer marker present in the test subject-derived sample.

Examples of the qualitative detection of the epithelial ovarian cancer marker include detection by an immunohistochemical method or Western blotting.

In the case of quantitatively detecting the epithelial ovarian cancer marker, for example, by immunoassay, epithelial ovarian cancer is diagnosed on the basis of the quantitative assay results. When the measurement value of the B3GNT3 polypeptide fragment is equal to or higher than a predetermined value, the test subject is diagnosed to be likely to have epithelial ovarian cancer.

In the present specification, the "measurement value" refers to a value obtained by the above assay method and may be an absolute value such as concentration or may be a relative value such as signal intensity from the epithelial ovarian cancer marker per unit sample.

Usually, the glycosyltransferase B3GNT3 polypeptide fragment found as an epithelial ovarian cancer marker by the present inventors is rarely detected in a sample derived from a normal individual. Thus, the test subject can be diagnosed to be likely to have epithelial ovarian cancer as a rule provided that the B3GNT3 polypeptide fragment of interest is detected.

If more highly precise diagnosis is desired, a method based on the measurement value is preferred. Specifically, when the B3GNT3 polypeptide fragment is detected by the assay method with a measurement value equal to or higher than a predetermined value, the test subject can be diagnosed to be likely to have epithelial ovarian cancer. The "predetermined value" refers to a measurement value capable of separating epithelial ovarian cancer patients from normal individuals, for example, a cutoff value. Specifically, examples of the predetermined value in the case of using the anti-epithelial ovarian cancer marker antibody of the present invention include a cutoff value mentioned later.

The anti-epithelial ovarian cancer marker antibody used, however, may have cross reactivity, albeit slightly, and detect other glycosyltransferases. Alternatively, nonspecific reaction derived from impurities may not be eliminated for normal individuals or patients with cancer other than epithelial ovarian cancer. In such cases, only the detection of the presence or absence of the epithelial ovarian cancer marker might not achieve accurate diagnosis.

Thus, for example, if the anti-epithelial ovarian cancer marker antibody used may have cross reactivity, the epithelial ovarian cancer marker can be detected by the sandwich method to thereby enhance its specificity and also significantly reduce the nonspecific reaction derived from impurities. The GT117-2 antibody, and the GT117-3 antibody of the present invention have been confirmed to exhibit no cross reactivity.

If there is the possibility that the epithelial ovarian cancer marker of the present invention is detected even in a normal individual, the presence or absence of epithelial ovarian cancer may be diagnosed on the basis of a statistically significantly high measurement value of the epithelial ovarian cancer marker in the test subject-derived sample compared with that in the normal individual. The value of the epithelial ovarian cancer marker obtained by the above quantitative method can be used as the measurement value of the epithelial ovarian cancer marker. In this case, a protein known in the art expected to have no quantitative difference between the samples of the test subject and the normal individual can be used as an internal control to correct the quantitative detection results of the test subject and the normal individual. Thus, the amount of the epithelial ovarian cancer marker can be obtained more accurately. Examples of such internal control proteins include albumin.

The term "statistically significantly" means that the test subject and the normal individual exhibit significant difference therebetween when the quantitative difference in the epithelial ovarian cancer marker contained in their samples is statistically treated. Specifically, examples of the significant difference include difference with a significance level smaller than 5%, 1%, or 0.1%. A test method known in the art capable of determining the presence or absence of significance can be appropriately used as a testing method for the statistical treatment without particular limitations. For example, the student's t test or multiple comparison test method can be used. The term "statistically significantly high" specifically means that the obtained value is higher than a cutoff value defined as a value capable of separating individuals having epithelial ovarian cancer from normal individuals, etc. such that sensitivity and specificity set by a routine method in multiple-specimen analysis are optimized.

In the case of using, for example, the GT117-2 antibody and the GT117-3 antibody as the anti-epithelial ovarian cancer marker antibodies in the sandwich method according to the present invention, the cutoff value at which individuals having epithelial ovarian cancer are separated from normal individuals is 24 ng/mL (the optimal threshold point in the drawn ROC curve of the peritoneal lavage fluids of ovarian cancer patients vs. the peritoneal lavage fluids of disseminated gastric cancer patients), preferably 35 ng/mL (the upper 95 percentile of the peritoneal lavage fluids of disseminated gastric cancer patients), more preferably 58 ng/mL (the lower 95 percentile of the peritoneal lavage fluids of ovarian cancer patients). Thus, when the measurement value of the epithelial ovarian cancer marker in the test subject-derived sample is higher than the cutoff value, the test subject can be diagnosed to have epithelial ovarian cancer.

In addition to the epithelial ovarian cancer marker B3GNT3 polypeptide fragment of the present invention, two or more additional epithelial ovarian cancer markers may be further used to diagnose epithelial ovarian cancer developed in the test subject. The detection of a plurality of different epithelial ovarian cancer markers in the sample of the test subject can further reduce a false positive rate and a false negative rate and achieve more highly precise diagnosis of epithelial ovarian cancer.

The "additional epithelial ovarian cancer marker" is not particularly limited as long as the marker is a biological marker other than the B3GNT3 polypeptide fragment for detection of epithelial ovarian cancer and is a biomaterial serving as an index showing that a test subject has epithelial ovarian cancer. Since the epithelial ovarian cancer marker of the present invention is a glycosyltransferase-derived polypeptide, the additional epithelial ovarian cancer marker may also be a glycosyltransferase-derived polypeptide. Examples of the glycosyltransferase-derived polypeptide other than B3GNT3 that may serve as an epithelial ovarian cancer marker include polypeptide fragments based on each of β1,6-N-acetylglucosaminyltransferase 5B (hereinafter, also abbreviated to "MGAT5B" in the present specification), and β1,3-galactosyltransferase 5, β1,3-galactosyltransferase 4, and N-acetylglucosamine-6-O-sulfotransferase 2 described in Patent Literature 2. Among them, a polypeptide fragment based on MGAT5B can be preferably used in combination with the polypeptide fragment based on B3GNT3.

"β1,6-N-acetylglucosaminyltransferase 5B (MGAT5B)" refers to a glycosyltransferase that has been newly found by the present inventors together with B3GNT3 and can serve as an epithelial ovarian cancer marker. MGAT5B is a membrane protein localized in the Golgi membrane and one type of N-linked sugar chain-synthesizing enzyme. This enzyme transfers N-acetylglucosamine with the β1-6 linkage (Kaneko M. et al., 2003, FEBS Letters, 554: 515-519). As with B3GNT3, MGAT5B contains one N-terminal transmembrane domain and has an enzymatically active region as a C-terminal region. Thus, the whole or a part of a polypeptide region corresponding to the C-terminal region of MGAT5B or its natural variant can be used as the "additional epithelial ovarian cancer marker". The MGAT5B according to the present invention is the human-derived wild-type MGAT5B composed of 790 amino acids and registered under GenBank Accession No. NP_653278. Specifically, the MGAT5B according to the present invention is a polypeptide consisting of the amino acid sequence represented by SEQ ID NO: 4. In this polypeptide, the region that can serve as the additional epithelial ovarian cancer marker is a MGAT5B polypeptide fragment consisting of the whole or a part of a polypeptide region consisting of the amino acid sequence represented by SEQ ID NO: 3.

Examples of the antibody that specifically recognizes and binds to the MGAT5B polypeptide fragment include an anti-MGAT5B antibody that recognizes, as an epitope, a part of the amino acid sequence represented by SEQ ID NO: 3 in MGAT5B. Specific examples thereof include a GT131-2 antibody, a GT131-7 antibody, a GT131-12 antibody, and a GT131-18 antibody. Hybridomas GT131-2, GT131-7, GT131-12, and GT131-18 respectively producing these anti-MGAT5B antibodies were nationally deposited on Apr. 4, 2011 with International Patent Organism Depositary, National Institute of Advanced Industrial Science and Technology (Tsukuba Central 6, 1-1-1 Higashi, Tsukuba, Ibaraki, Japan) and internationally deposited on the same date with International Patent Organism Depositary, National Institute of Technology and Evaluation (Tsukuba Central 6, 1-1-1 Higashi, Tsukuba, Ibaraki. Japan (post code: 305-8566)). These hybridomas are identified by International Accession Nos. FERM BP-11496 (National Deposition No: FERM P-22097) for GT131-2, FERM BP-11497 (National Deposition No: FERM P-22098) for GT131-7, FERM BP-11498 (National Deposition No: FERM P-22099) for GT131-12, and FERM BP-11499 (National Deposition No: FERM P-22100) for GT131-18. In this respect, other antibodies that may be used are a recombinant antibody comprising light chain CDRs and heavy chain CDRs of the anti-MGAT5B antibody, and a fragment of the anti-MGAT5B antibody or the recombinant antibody comprising light chain CDRs and heavy chain CDRs of the anti-MGAT5B antibody, the fragment having the activity of recognizing MGAT5B. The antibody, the recombinant antibody, or the antibody fragment can be used to quantitatively and/or qualitatively detect the epithelial ovarian cancer marker from the sample of the same test subject in the same way as in the anti-B3GNT3 antibody or the like.

The epithelial ovarian cancer marker of the present invention as well as the additional epithelial ovarian cancer marker such as the MGAT5B polypeptide fragment is detected from the sample of the same test subject to diagnose epithelial ovarian cancer developed in the test subject. When both of the epithelial ovarian cancer markers can be detected, the test subject can be diagnosed to be more likely to have epithelial ovarian cancer. Only one of the epithelial ovarian cancer markers may be detected, while the other epithelial ovarian cancer marker may not be detected. This suggests that either of the markers has produced wrong detection results. In this case, the markers can each be detected again by the sandwich method and/or the markers can each be tested for whether their measurement values exceed the cutoff values. As a result, the presence or absence of epithelial ovarian cancer developed in the test subject can be diagnosed on the basis of the results obtained using the more reliable marker. Alternatively, the second additional epithelial ovarian cancer marker may be detected in the sample by the same method as above, and the presence or absence of epithelial ovarian cancer developed in the test subject can be diagnosed on the basis of more consistent results among the detection results of these three epithelial ovarian cancer markers.

The quantitative and/or qualitative detection of two or more different epithelial ovarian cancer markers can further reduce a false negative rate and/or a false positive rate and also enhance the diagnosis precision.

EXAMPLES

Example 1: Preparation of Anti-B3GNT3 Antibody and Hybridoma Producing the Antibody 1. Selection and Preparation of Immunogen An immunogen B3GNT3 gene was selected by real-time PCR analysis on transcripts of a total of 186 glycosyltransferases known in the art in ovarian cancer cell lines RMG-I, RMG-II, and RMG-V (all derived from clear cell adenocarcinoma), RMUG-S (derived from mucinous adenocarcinoma), peripheral blood cells, and normal tissues of the large intestine, the liver, and the stomach. Specifically, their transcription levels in the ovarian cancer cell lines and the normal tissues were ranked by the comparison of mean values and the comparison of maximum values to select a top glycosyltransferase as an ovarian cancer marker candidate. B3GNT3, one of the selected candidates, was ranked in 12th in terms of the mean value and in 6th in terms of the maximum value and placed in a higher rank than that of GAT (mean value: No. 14 and maximum value: No. 13) and β1,3-galactosyltransferase 4 (mean value: No. 32 and maximum value: No. 17). In addition, B3GNT3 was detected at a high transcription level even in a mucinous ovarian cancer cell line (RMUG-S), which had a high tendency to show negative for CA125, GAT, or the like. For these reasons, B3GNT3 was selected as a promising marker candidate specific for ovarian cancer.

For the expression of the B3GNT3 gene, a B3GNT3 expression vector was prepared on the basis of pIRESpuro3 (Clontech Laboratories, Inc.). First, pIRESpuro3 was cleaved with NruI and BamHI. On the other hand, pFC3 (Promega K.K.) was cleaved with FspI and BamHI. The obtained fragment was incorporated into the NruI/BamHI-cleaved pIRESpuro3 to obtain pIRES-F-puro3. The plasmid pIRES-F-puro3 has sequences encoding preprotrypsin (MSALLILALVGAAVA: SEQ ID NO: 5) and a FLAG tag sequence (DYKDDDDK: SEQ ID NO: 6) downstream of an expression promoter derived from pFC3 and contains EcoRI and EcoRV as a multicloning site further downstream thereof.

A plasmid containing a full-length human B3GNT3 gene sequence (SEQ ID NO: 7) was obtained by a method described in Non Patent Literature (Shiraishi N. et al., 2001, J. Biol. Chem. 276:3498-3507). This plasmid was used as a template in PCR amplification using primer A (taggaattc-cGAGCAGCCAC: SEQ ID NO: 8) and primer B (cgcg-gatccTCAGTAGATCT: SEQ ID NO: 9). This PCR was performed by 30 cycles each involving 94° C. for 30 seconds, then 55° C. for 30 seconds, and 68° C. for 30 seconds. The amplification product was purified using Qiagen Minielute Kit, then digested with EcoRI and BamHI, and inserted to a similarly digested pIRES-F-puro3 (pIRES-F-puro3-B3GNT3). The obtained plasmid pIRES-F-puro3-B3GNT3 encodes a fusion protein (soluble B3GNT3 polypeptide fragment) composed of: a region from Gln 38 to 372 Tyr in B3GNT3 represented by SEQ ID NO: 1; and preprotrypsin, FLAG, and LAAANSE (linker) linked to the N-terminus thereof. The preprotrypsin sequence is cleaved off during secretion from cells.

pIRES-F-puro3-B3GNT3 was transferred to *E. coli* DH5α and subcloned therein, followed by transfection of HEK293T by a routine method using Lipofectamine 2000. A stably expressing strain was obtained by selection in the presence of 10 μg/mL puromycin. The soluble B3GNT3 polypeptide fragment of interest was recovered using Anti-FLAG M2 Affinity Gel (A2220; Sigma-Aldrich Corp.). Its expression was then detected by SDS-PAGE and confirmed by Western blotting using Monoclonal Anti-FLAG M2 Antibody Affinity purified (F1804; Sigma-Aldrich Corp.).

For the large-scale preparation of the soluble B3GNT3 polypeptide fragment, the strain was cultured at 37° C. in 1500 mL of a medium (DMEM high glucose, 10% FBS, 10 μg/mL puromycin, 500 U/mL penicillin, 10 μg/mL streptomycin). The culture was started at 15% confluence and continued for approximately 2 days. Then, the culture supernatant was recovered in a 70% confluent state.

Insoluble residues were removed from the obtained culture supernatant using Nalgene PES Bottle Top Filter 0.45 μm cut-off. 1.5 mL of anti-FLAG M2 Affinity Gel (Sigma-Aldrich Corp.) was added into the sample, and the mixture was left with stirring at 4° C. The resin was recovered, then packed into an empty column, and washed with 25 mL of PBS, followed by elution using 1 mL of a FLAG peptide (manufactured by Sigma-Aldrich Corp.) dissolved at a concentration of 1 g/mL in PBS. The eluted fraction was concentrated into 500 μL by ultrafiltration and subsequently applied to a Superdex 200 10/300 GL (GE Healthcare Japan Corp.) gel filtration column equilibrated in advance with a buffer solution (20 mM Tris-HCl, 50 mM NaCl, pH 8.0). 250 μL each of fractions was separated, and each fraction was electrophoresed to obtain a fraction containing the soluble B3GNT3 polypeptide fragment. These fractions were combined and then concentrated into 2.5 mg/mL with the solvent replaced with PBS to obtain a soluble B3GNT3 polypeptide fragment preparation. This preparation was used as an immunogen.

2. Immunization and Cell Fusion

50 μg of the soluble B3GNT3 polypeptide fragment thus prepared as an immunogen was dissolved in 0.1 mL of saline and then supplemented and fully mixed with 0.1 mL of a Freund's complete adjuvant to prepare an emulsion. 0.2 mL of the emulsion was subcutaneously injected to the back of a Balb/c mouse (9-week-old female). 0.05 mL of an aluminum adjuvant was added to an immunogen solution containing 25 μg of the immunogen dissolved in 0.05 mL of saline, and fully mixed, and the resulting emulsion was intraperitoneally injected to the mouse 1 week after the initial immunization. A solution containing 50 μg of the immunogen dissolved in 0.1 mL of saline and a solution containing 25 μg of the immunogen dissolved in 0.05 mL of saline were further intraperitoneally injected to the mouse 4 weeks after the initial immunization and 5 weeks after the initial immunization, respectively.

Three days after the final immunization, the spleen was excised from the mouse, and extracted spleen cells were washed with an RPMI1640 medium. A suspension of 1.2× 10^8 spleen cells and a suspension of 3×10^7 mouse myeloma cells (P3/X63-Ag8.U1) were mixed and centrifuged, followed by removal of the medium. 2 mL of polyethylene glycol/RPMI1640 medium heated to 37° C. was gradually added to the cells, which were then fused by mild stirring. Then, the medium was removed by centrifugation, and 20% S-Clone/Cloning Medium (Sanko Junyaku Co., Ltd.) and 60 mL of an RPMI1640 medium containing 10% FBS were added to the cells. Subsequently, the mixture was dispensed at a volume of 0.1 mL/well to a 96-well plate. Four hours later, a HAT medium (HAT medium×1 concentration: 0.1 mM hypoxanthine, 0.4 μM aminopterin, 16 μM thymidine, 20% S-Clone, RPMI1640 medium containing 10% FBS) adjusted to twice the usual concentration was added thereto at a volume of 0.1 mL/well. The medium in each well was replaced by half with a fresh one 2 days and 4 days after the fusion. After 10-day culture, hybridoma growth was observed in approximately 80% of the wells.

3. Selection of Hybridoma

For screening for an antibody in each hybridoma culture supernatant, study was made using ELISA with the B3GNT3 polypeptide fragment prepared in the paragraph "1. Selection and preparation of immunogen" as an antigen. First, the antigen was adsorbed at a concentration of 1 μg/mL in PBS onto a microtiter plate for ELISA. The plate was blocked with PBS containing 5% sucrose and 5% Tween 20 and then reacted with the hybridoma culture supernatant. The plate was further reacted with a peroxidase-labeled goat anti-mouse immunoglobulin antibody. The absorbance was measured at 450 nm using 3,3',5,5'-tetramethylbenzidine (TMB) as a substrate to detect the antibody of interest. As a result, antibody-producing hybridomas were obtained in a total of 18 wells. These hybridomas were each transferred to an HT medium (HAT medium except for aminopterin), further transferred to an RPMI1640 medium containing 10% FBS, and cultured.

Next, the hybridomas were cloned by the limiting dilution method. Each hybridoma was diluted into a density of approximately 1 cell/well in a 96-well plate and cultured in an RPMI1640 medium containing 15% FBS. Approximately 10 days later, the growth and number of colonies in the wells were confirmed by microscopic examination. Approximately 14 days later, 0.1 mL of each culture supernatant was recovered and used to select antibody-producing cells by ELISA.

Also, reactivity with impurities that might be contained in the immunogen was confirmed by ELISA. FBS for culture used in the paragraph "1. Selection and preparation of immunogen" and an arbitrary polypeptide fragment (different from the immunogen) expressed using the same vector as in the FLAG-B3GNT3 polypeptide fragment were each adsorbed at a concentration of 2 μg/mL in PBS onto a microtiter plate for ELISA. Hybridomas whose culture supernatants reacted therewith were discarded. In this way, 2 stable monoclonal antibody-producing hybridomas GT117-2 and GT117-3 were obtained as a result of cloning. The immunoglobulin subclasses of the monoclonal antibodies produced by these hybridomas were determined using a mouse monoclonal antibody isotyping kit (AbD Serotec, A Bio-Rad Company). All of these antibodies were IgG1, κ.

Monoclonal antibodies were prepared in large amounts from 2 anti-B3GNT3 monoclonal antibody-producing hybridomas (GT117-2 and GT117-3) obtained above. Specifically, each hybridoma was expanded into 100 mL in an RPMI1640 medium containing 10% FBS and recovered at the logarithmic growth phase. The cells were dispersed in 2% FBS and 500 mL of an RPMI1640 medium containing ITS-A (10 mg/L insulin, 6.7 mg/L sodium selenate, 5.5 mg/L transferrin, 11.0 mg/L sodium pyruvate) and rotary cultured in a roller bottle. At day 2 and day 4 after the start of the rotary culture, the cells were further diluted twice with an ITS-A-containing RPMI1640 medium and maintained until day 10 to day 14. Finally, a culture supernatant derived from 1% FBS and 1 L of the ITS-A-containing RPMI1640 medium was obtained in two roller bottles. The cells were removed by centrifugation and filtration. Then, NaCl, glycine, sodium azide, and sodium hydroxide were added to the supernatant to adjust pH at 8.9, containing 3 M NaCl, 1.5 M glycine, and 0.1% sodium azide. Then, the culture supernatant was applied to a protein A-Sepharose affinity column, 4 mL (GE Healthcare Japan Corp.) equilibrated with the same buffer solution as above (containing 3 M NaCl, 1.5 M glycine, and 0.1% sodium azide, pH 8.9) to bind the antibody to the column. Next, the column was washed with the above buffer solution in an amount of 20 times the column, followed by elution with a 0.1 M citrate buffer solution (pH 6.0) containing 0.1% sodium azide. Peaks were fractionated using a fraction collector. Each peak fraction thus obtained was recovered and then salted out with 50% saturated ammonium sulfate. After centrifugation, the precipitate was dissolved in a 50 mM tris buffer solution (pH 8.0) containing 0.15 M NaCl and 0.1% sodium azide. In this way, approximately 10 to 40 mg of purified IgG was obtained from each of the 2 hybridomas.

Example 2: Confirmation of Antigen Specificity of Monoclonal Antibody

The hybridoma-derived anti-B3GNT3 monoclonal antibodies (GT117-2 antibody and GT117-3 antibody) obtained in Example 1 were studied for their antigen specificity.
(Method)
2 ng of the FLAG-B3GNT3 polypeptide fragment obtained in Example 1, 2 ng of the B3GNT3 polypeptide fragment obtained by the cleavage of the FLAG tag from the fragment through enzymatic treatment, 5 µL of a culture supernatant (supernatant obtained by: incorporating the inserted fragment of pIRES-F-puro3-B3GNT3 into a pET20b vector for secretion; transferring the obtained vector for expression to an *E. coli* BL21 strain; and performing induction treatment by a routine method using IPTG) of *E. coli* allowed to express an untagged recombinant B3GNT3 polypeptide fragment, and 0.1 µL of pool normal human serum (NHS) containing a serum mixture from a plurality of healthy adults were each electrophoresed using a 10% polyacrylamide gel under SDS-PAGE reduced conditions and transferred to a PVDF membrane. Each membrane was blocked with PBS containing 5% skimmed milk and then reacted with each purified monoclonal GT117-2 antibody (1 µg/mL) and GT117-3 antibody (0.5 µg/mL) at room temperature for 90 minutes. After washing, the membrane was soaked with an HRP-labeled anti-mouse IgG antibody (GE Healthcare Japan Corp.) as a secondary antibody and reacted at room temperature for 60 minutes. After washing, the antigen-antibody binding was detected on the basis of chemiluminescence using a Western blotting detection reagent (PerkinElmer Inc.).
(Results)
The results are shown in FIG. 1. The GT117-2 antibody and the GT117-3 antibody were both confirmed to bind to the FLAG-B3GNT3 polypeptide fragment and the B3GNT3 polypeptide fragment from which the FLAG tag was cleaved off. By contrast, these antibodies exhibited no reactivity with the NHS. These results demonstrated that the GT117-2 antibody and the GT117-3 antibody specifically react with the B3GNT3 polypeptide fragment and do not react with other proteins contained in human serum. The GT117-3 antibody was confirmed to also react with the culture supernatant of expressing *E. coli*. Unlike B3GNT3 in human cells, the recombinant B3GNT3 polypeptide fragment expressed in *E. coli* is unglycosylated. These results demonstrated that the GT117-3 antibody is capable of recognizing the B3GNT3 polypeptide fragment of interest, regardless of the presence or absence of glycosylation.

Figure 2:
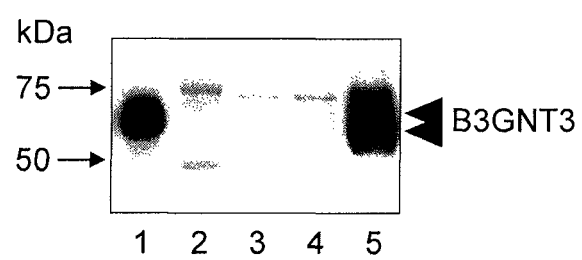
FIG. 2 shows results of detecting a B3GNT3 polypeptide fragment in a sample of a test subject and a culture supernatant of an ovarian cancer cell line by Western blotting using an anti-B3GNT3 monoclonal antibody. Lane 1 shows the results about a purified recombinant B3GNT3 polypeptide fragment. Lane 2 shows the results about a peritoneal lavage fluid collected from an ovarian cancer patient. Lanes 3 to 5 each show the results about the culture supernatant of an ovarian cancer cell line (derived from an RMG-I cell line, an RMG-V cell line, and an RMUG-S cell line, respectively).

Example 3: Detection of B3GNT3 Polypeptide Fragment in Sample of Test Subject and Culture Supernatant of Epithelial Ovarian Cancer Cell Line Using Anti-B3GNT3 Antibody of the Present Invention The GT117-3 antibody obtained in Example 1 was confirmed for its ability to detect the epithelial ovarian cancer marker B3GNT3 polypeptide fragment of the present invention in samples of test subjects (peritoneal lavage fluids of epithelial ovarian cancer patients) and culture supernatants of epithelial ovarian cancer cell lines.
(Method)
Peritoneal lavage fluids collected from epithelial ovarian cancer patients, culture supernatants of three ovarian cancer cell lines (RMG-I, RMG-V, and RMUG-S), and the FLAG-B3GNT3 polypeptide fragment as a control were each electrophoresed on a 10% polyacrylamide gel and transferred to a PVDF membrane. Each membrane was blocked with PBS containing 5% skimmed milk. The membrane was reacted with the GT117-3 antibody (1 µg/mL) labeled using a biotin labeling kit (Dojindo Laboratories) at room temperature for 2 hours. Then, the membrane was washed and reacted with HRP-labeled streptavidin (GE Healthcare Japan Corp.) at room temperature for 60 minutes. The membrane was further washed and then subjected to detection based on chemiluminescence using a Western blotting detection reagent (PerkinElmer Inc.).
(Results)
The results are shown in FIG. 2. A smear band presumed to be the B3GNT3 polypeptide fragment was detected (arrowhead) using the GT117-3 antibody from the peritoneal lavage fluids of epithelial ovarian cancer patients and the culture supernatants of the epithelial ovarian cancer cell lines RMG-V and RMUG-S. These results suggested the possibility that the B3GNT3 polypeptide fragment is secreted from an epithelial ovarian cancer cell line and also secreted into the peritoneal lavage fluid of an epithelial ovarian cancer patient. Particularly, the GT117-3 antibody strongly reacted with the culture supernatant of the mucinous ovarian cancer cell line RMUG-S, and the expression level detected in Example 1 was actually reflected in the amount of the peptide fragment extracellularly secreted, demonstrating that the B3GNT3 polypeptide fragment is secreted at a high concentration.

Example 4: Detection of B3GNT3 Polypeptide Fragment by Immunoprecipitation Using Anti-B3GNT3 Antibody (Method)
The pool NHS was diluted 100-fold with a 50 mM tris buffer solution (pH 8.0) containing 0.15 M NaCl and 0.1% sodium azide. The FLAG-B3GNT3 polypeptide fragment prepared in Example 1 was added thereto at a final concentration of 10 µg/mL. This mixture was used as an immunoprecipitation sample. 2 µg of each monoclonal antibody GT117-2 antibody, or GT117-3 antibody and 20 µL of a protein G gel (GE Healthcare Japan Corp.) were added to 0.5 mL of this sample and mixed at 4° C. for 4 hours using a rotator. The sample solution was discarded by centrifugation, and the protein G gel was washed with the above tris buffer solution. Then, 40 μL of an SDS-PAGE sample buffer was added thereto, and the mixture was heated at 98° C. for 5 minutes to obtain immunoprecipitated fractions.

Subsequently, the FLAG-B3GNT3 polypeptide fragment, each fraction immunoprecipitated with the GT117-2 antibody, and the GT117-3 antibody, and a mixture of a non-immunoprecipitated pool NHS and the FLAG-B3GNT3 polypeptide fragment were each electrophoresed using a 10% polyacrylamide gel under SDS-PAGE reduced conditions and transferred to a PVDF membrane. Each membrane was blocked with PBS containing 5% skimmed milk and then reacted with an HRP-labeled anti-FLAG antibody (M2, Sigma-Aldrich Corp.) at room temperature for 1 hour. Alternatively, the membrane was reacted with the GT117-2 antibody (1 μg/ml) or the GT117-3 antibody (0.5 μg/ml) labeled using a biotin labeling kit (Dojindo Laboratories) at room temperature for 2 hours. After washing, the membrane was reacted with HRP-labeled streptavidin (GE Healthcare Japan Corp.) at room temperature for 60 minutes. These PVDF membranes were washed and then subjected to detection based on chemiluminescence using a Western blotting detection reagent (PerkinElmer Inc.).
(Results)

Figure 3:
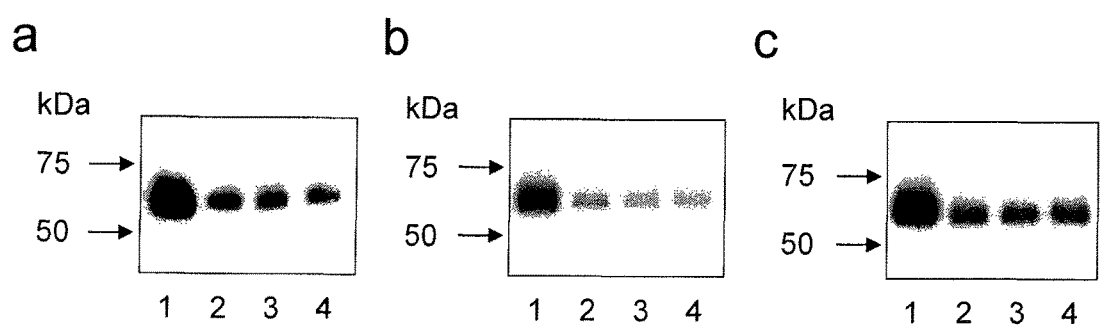
FIG. 3 shows results of Western blotting by which FLAG-B3GNT3 polypeptide fragments immunoprecipitated with anti-B3GNT3 antibodies were detected using various antibodies (a: anti-FLAG antibody, b: GT117-2 antibody, and c: GT117-3 antibody). Lane 1 shows the results about a control FLAG-B3GNT3 polypeptide fragment. Lane 2 shows the results about a sample obtained by the immunoprecipitation with a GT117-2 antibody of a FLAG-B3GNT3 polypeptide fragment mixed with the NHS. Lane 3 shows the results about a sample obtained by the immunoprecipitation with a GT117-3 antibody of a FLAG-B3GNT3 polypeptide fragment mixed with the NHS. Lane 4 shows the results about a non-immunoprecipitated FLAG-B3GNT3 polypeptide fragment mixed with the NHS.

The results are shown in FIG. 3. The FLAG-B3GNT3 polypeptide fragment added as an immunoprecipitation sample was detected from all of the immunoprecipitated fractions. These results showed that the monoclonal antibody of the present invention, i.e., the GT117-2 antibody, and the GT117-3 antibody is capable of specifically immunoprecipitating the B3GNT3 polypeptide fragment even from a protein solution rich in impurities, such as serum.

Example 5: Immunostaining of Ovarian Cancer Cell Line Using Anti-B3GNT3 Antibody An ovarian cancer cell line was immunostained using the anti-B3GNT3 monoclonal antibodies (GT117-2 antibody and GT117-3 antibody) prepared in Example 1.
(Method)

The culture supernatant (containing the GT117-2 antibody) of the GT117-2 producing hybridoma, the culture supernatant (containing the GT117-3 antibody) of the GT117-3 producing hybridoma, or an anti-B4GALT1 monoclonal antibody MAb8628 (Uemura M. et al., 1992, Cancer Res., 52: 6153-6157) for use as a trans-Golgi marker was added to an epithelial ovarian cancer cell line RMUG-S and reacted overnight at 4° C. Then, the binding reaction of the antibodies with various glycosyltransferases was visualized using Alexa 488-labeled anti-mouse IgG (Life Technologies Corp.). The nuclei were stained with Hoechst 33342 (Life Technologies Corp.). Images were taken using a Keyence microscope BioZero.
(Results)

Figure 4:
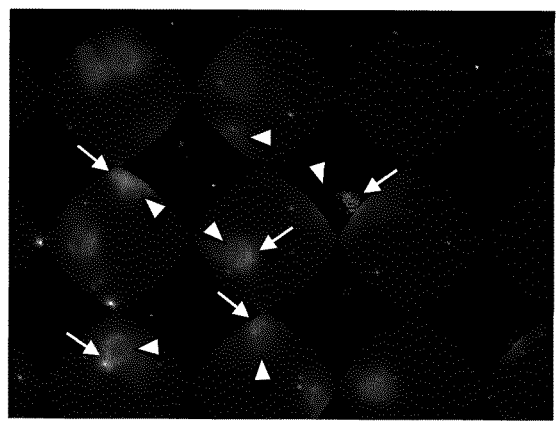
FIG. 4 shows the immunostaining of an ovarian cancer cell line using anti-B3GNT3 antibodies.
Figure 4:
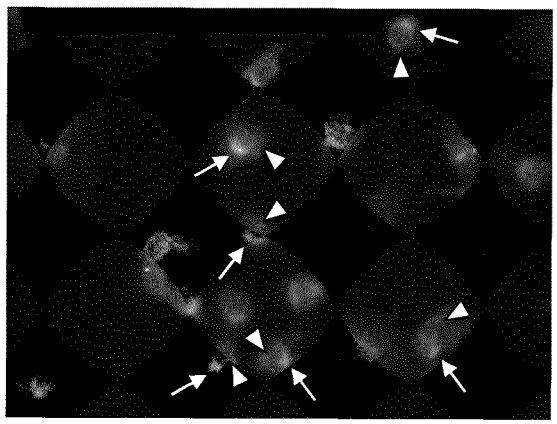
Figure 4:
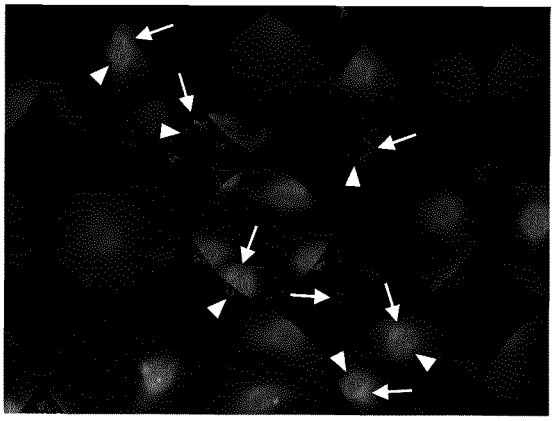

The results are shown in FIG. 4. FIG. 4a is a staining pattern of the epithelial ovarian cancer cell line RMUG-S immunostained with the GT117-2 antibody. FIG. 4b is a staining pattern of the cell line immunostained with the GT117-3 antibody. FIG. 4c is a staining pattern of the cell line immunostained with the staining positive control anti-B4GALT1 antibody. The antibody-stained part is indicated by an arrow, and the nuclear-stained part is indicated by an arrowhead. From these results, the GT117-2 antibody and the GT117-3 antibody were both confirmed to be capable of staining the epithelial ovarian cancer cells in a manner specific for the epithelial ovarian cancer marker. The intracellular localization pattern of the glycosyltransferase detected with the anti-B4GALT1 antibody was the same as that of the glycosyltransferase detected with the GT117-2 antibody or the GT117-3 antibody. This suggests that B3GNT3 is a glycosyltransferase localized to the Golgi bodies. These results showed that the GT117-2 antibody and the GT117-3 antibody of the present invention can be used in the staining of epithelial ovarian cancer cells and tissues.

Example 6: Selection of Antibody for Sandwich ELISA System (Method)

Two anti-B3GNT3 antibodies (GT117-2 antibody, and GT117-3 antibody) obtained in Example 1 were diluted into 5 μg/mL with PBS and added at a volume of 100 μL/well to a microplate for ELISA. Each antibody was adsorbed onto the plate overnight at 4° C. Then, the solution was discarded, and each well was washed. Next, PBS containing 3% bovine serum albumin (BSA) was added thereto as a blocking solution at a volume of 300 μL/well to block the plate. The blocking solution was discarded, and each well was washed. Then, 100 μL of a B3GNT3 polypeptide fragment solution adjusted to 0, 125, 500, and 2000 ng/mL was added to each well. After reaction at 37° C. for 2 hours, the solution in each well was discarded, and each well was washed. Then, GT117-2 antibody, and GT117-3 antibody labeled using a biotin labeling kit (Dojindo Laboratories) were each adjusted to 1 μg/mL and reacted therewith at room temperature for 2 hours. Then, the solution was discarded, and each well was washed. Then, a horseradish peroxidase (HRP)-labeled avidin (The Jackson Laboratory) solution was added thereto at a volume of 100 μL/well and reacted at room temperature for 1 hour. The reaction solution was discarded, and each well was washed. Then, color developed by a TMB substrate solution (Pierce Chemical Co.) was measured on the basis of absorbance at 450 nm. Among the combinations of two anti-B3GNT3 monoclonal antibodies (GT117-2 antibody and GT117-3 antibody) used, a system involving the GT117-3 antibody for immobilization and the GT117-2 antibody for detection exhibited a stable blank value and high sensitivity (data not shown). Thus, the GT117-3 antibody for immobilization on a microplate and the GT117-2 antibody for detection were used in the subsequent Examples as a preferred combination for detecting the B3GNT3 polypeptide fragment by a sandwich ELISA system.

Example 7: Construction of Highly Sensitive Sandwich CLEIA Assay System

In order to enhance the sensitivity of the sandwich ELISA system using the combination of the monoclonal antibodies selected in Example 6, i.e., the GT117-2 antibody and the GT117-3 antibody, the application of a chemiluminescent detection system (chemiluminescent enzyme immunoassay; CLEIA) was studied.
(Method)

The GT117-3 antibody of the present invention was adjusted to 4 μg/mL, then added at a volume of 100 μL/well to a 96-well microplate for fluorometric photometry (Nunc, Thermo Fisher Scientific Inc.), and immobilized thereon at room temperature for 7 hours. After discarding of the antibody solution, the plate was washed with PBS containing 0.05% Tween 20 and blocked overnight at 4° C. by the addition of a blocking solution (20 mM tris (pH 8.0) containing 0.2% highly pure casein (I-Block, Life Technologies Corp.), 0.1% Tween 20, and 0.15 M NaCl) at a volume of 300 μL/well. The B3GNT3 polypeptide fragment was adjusted as a concentration standard to 0, 12.5, 25, 50, 100, 200, 400, and 800 ng/mL with the above blocking solution. 10 μL of each concentration standard was added, together with 90 μL of the blocking solution, to each well of the microplate thus washed, and reacted at 37° C. for 2 hours. The plate thus reacted was washed five times with PBS containing 0.05% Tween 20. The GT117-2 antibody labeled with alkaline phosphatase using an alkaline phosphatase labeling kit (Dojindo Laboratories) was adjusted to 0.5 μg/mL with the above blocking solution, then added to the plate at a volume of 100 μL/well, and reacted at room temperature for 1.5 hours in the dark. The plate thus reacted was washed four times with PBS containing 0.05% Tween 20 and twice with 20 mM tris (pH 9.8) containing 1 mM magnesium chloride. A chemiluminescence reagent CSPD Substrate Sapphire-II (Life Technologies Corp.) was added thereto at a volume of 100 μL/well and reacted at room temperature in the dark. 45 minutes later, luminescence intensity was measured.

(Results)

Figure 5:
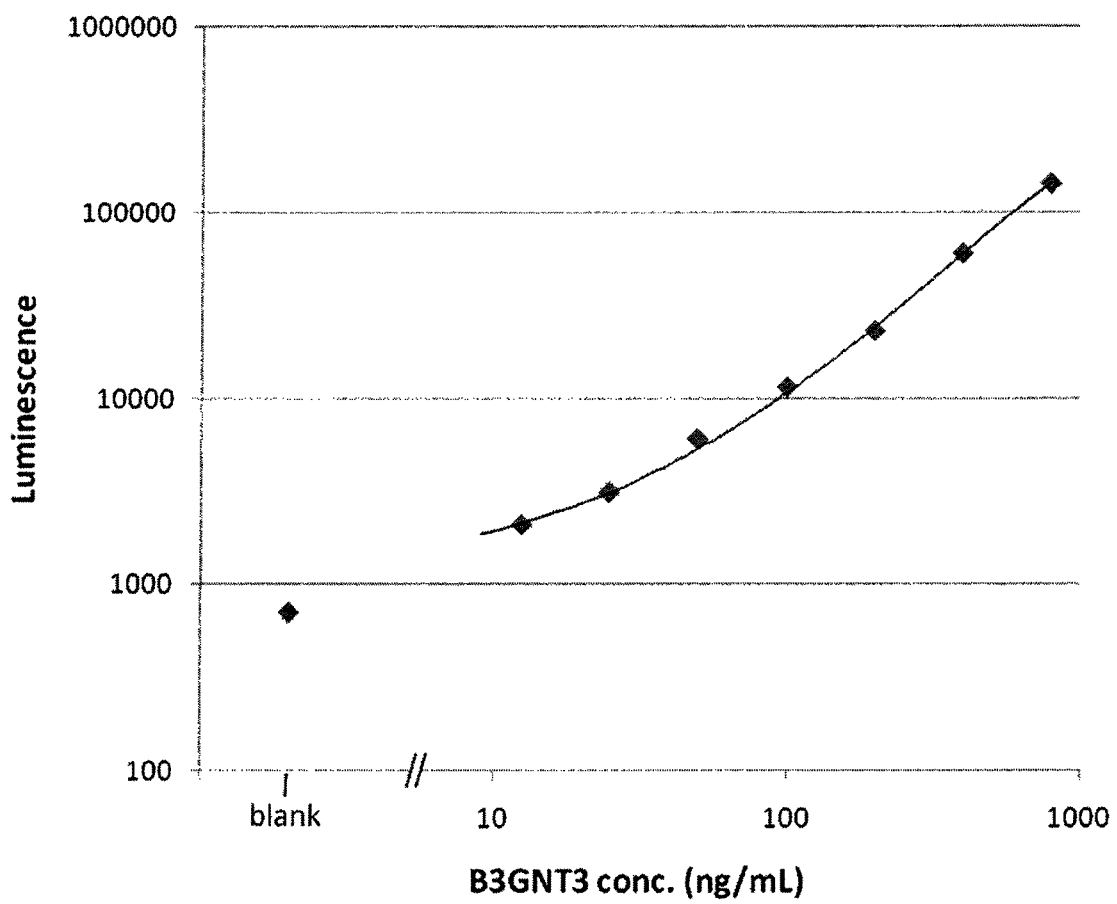
FIG. 5 shows a calibration curve of B3GNT3 polypeptide fragments obtained from values of a concentration standard measured by sandwich CLEIA using a GT117-2 antibody and a GT117-3 antibody.

FIG. 5 shows a calibration curve obtained from the measurement values of the concentration standard. Sandwich CLEIA using the GT117-2 antibody and the GT117-3 antibody of the present invention was confirmed to be capable of quantifying the glycosyltransferase B3GNT3 polypeptide fragment in a test subject-derived sample with detection sensitivity of approximately 10 ng/mL. The concentration of the B3GNT3 polypeptide fragment present in a sample obtained from a test subject can be determined using this calibration curve.

Example 8: Measurement of Amount of B3GNT3 Polypeptide Fragment in Peritoneal Lavage Fluid of Epithelial Ovarian Cancer Patient, Etc.

Method (1) Experimental Example 1

40 peritoneal lavage fluids collected from epithelial ovarian cancer patients as well as 55 peritoneal lavage fluids collected from patients with intraperitoneally disseminated gastric cancer and 159 peritoneal lavage fluids of patients with non-intraperitoneally-disseminated gastric cancer as control groups were used as samples in sandwich CLEIA using the calibration curve of the B3GNT3 polypeptide fragment obtained in Example 7. The concentration of the epithelial ovarian cancer marker (B3GNT3 polypeptide fragment) in each sample was quantitatively measured. The detailed assay method was performed according to the method described in Example 7.

(2) Comparative Example 1

40 peritoneal lavage fluids collected from the epithelial ovarian cancer patients used in Experimental Example 1 were used as samples to assay existing ovarian cancer markers CA125 and GAT in each sample. CA125 and GAT were assayed using Abnova CA125 (Human) ELISA kit (catalog No: KA0205) and Konica Minolta GAT Test Kit, respectively, according to the protocols attached thereto. The respective obtained measurement values of the markers were compared with the concentration measurement value of the B3GNT3 polypeptide fragment in 40 peritoneal lavage fluids of the ovarian cancer patients obtained in Experimental Example 1.

(Results)

Figure 6:
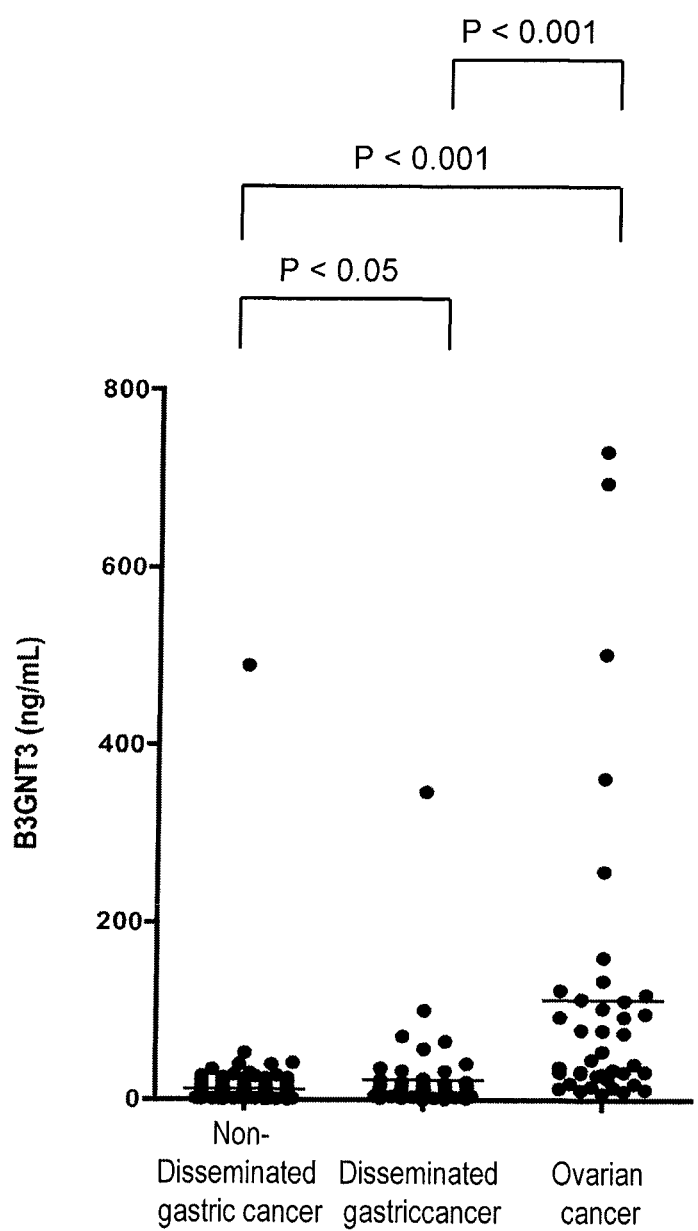
FIG. 6 shows the concentration of the epithelial ovarian cancer marker B3GNT3 polypeptide fragment of the present invention in a peritoneal lavage fluid collected from a test subject, wherein the concentration was measured by sandwich CLEIA using a GT117-2 antibody and a GT117-3 antibody.

The results of Experimental Example 1 are shown in FIG. 6. The results of Comparative Example 1 are shown in FIGS. 7 and 8.

First, referring to FIG. 6, the measurement values (epithelial ovarian cancer marker concentrations) were statistically analyzed and consequently significantly different among the above 3 groups. Particularly, the ovarian cancer group exhibited significantly high measurement values compared with two gastric cancer groups. The mean value thereof was 112.5 ng/mL in the specimens of the ovarian cancer patients, 21.9 ng/mL in the specimens of the disseminated gastric cancer patients, and 11.8 ng/mL in the specimens of the non-disseminated gastric cancer patients. These results demonstrated that sandwich CLEIA using the two anti-B3GNT3 antibodies of the present invention, i.e., the GT117-2 antibody and the GT117-3 antibody, with a cutoff value set to 24 ng/mL can determine epithelial ovarian cancer developed in the test subject from the sample derived therefrom with high accuracy rate of diagnosis.

Figure 7:
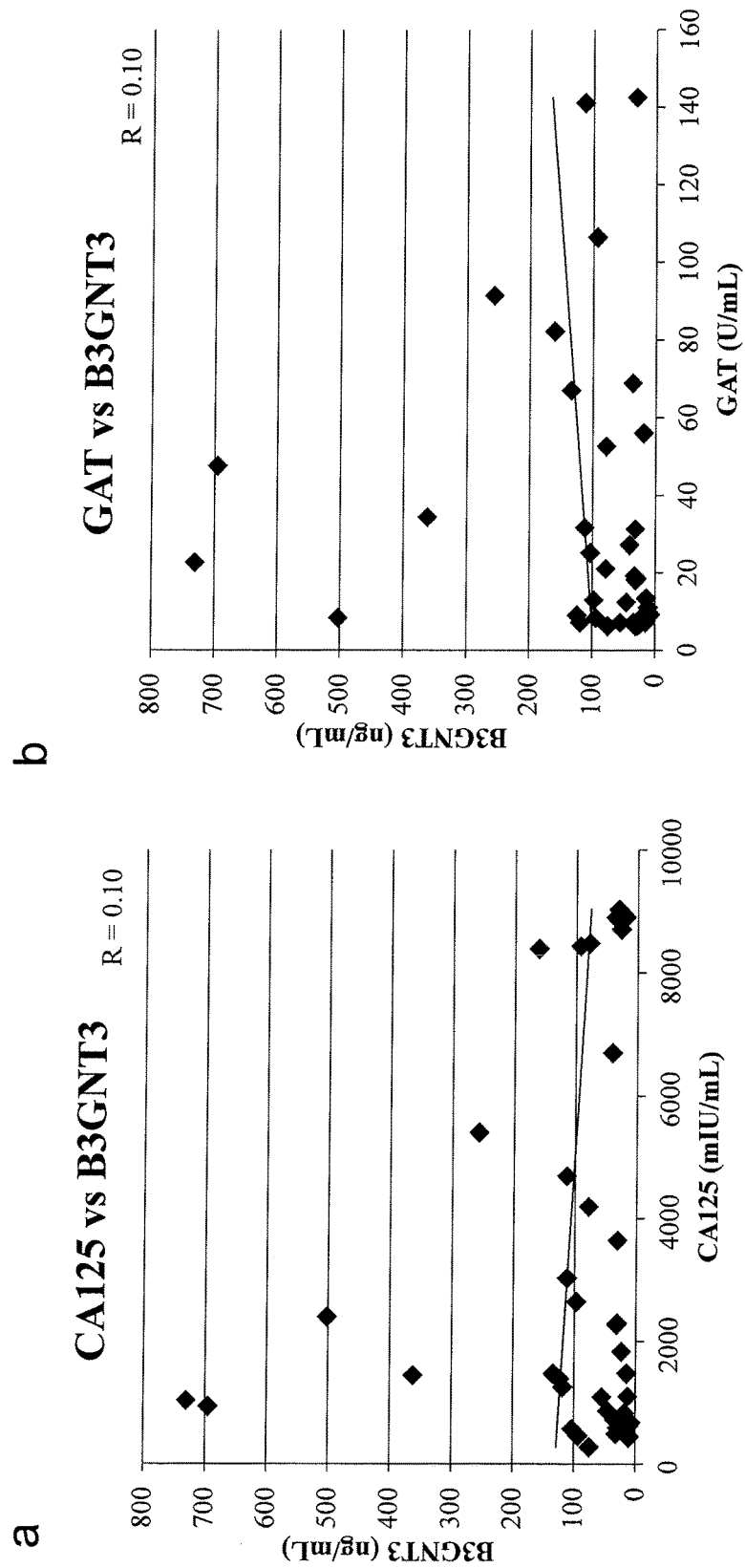
FIG. 7 shows the correlation between a measurement value of the B3GNT3 polypeptide fragment and a measurement value of an existing ovarian cancer marker CA125 (a) or GAT (b) in peritoneal lavage fluids collected from epithelial ovarian cancer patients.
Figure 8:
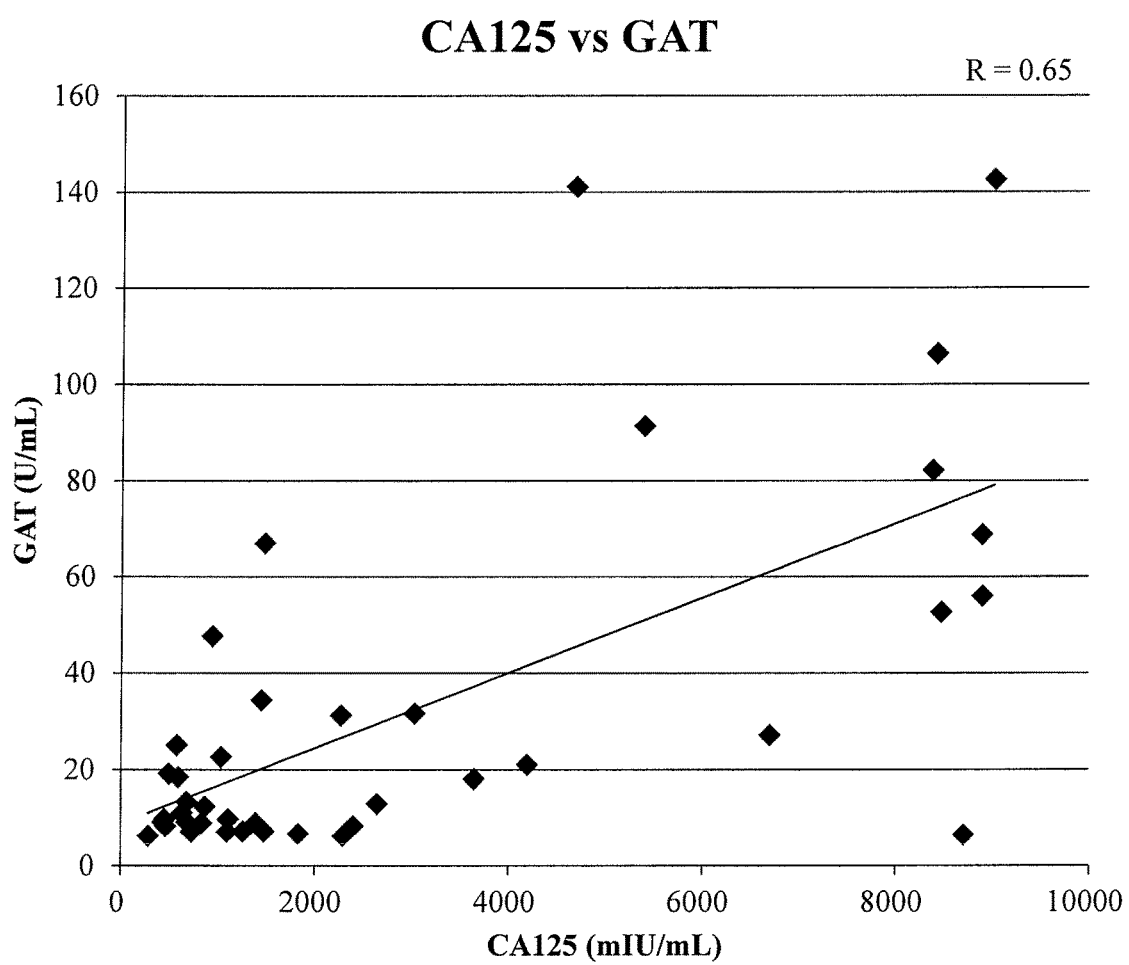
FIG. 8 shows the correlation between a CA125 measurement value and a GAT measurement value in peritoneal lavage fluids collected from epithelial ovarian cancer patients.

Next, referring to FIG. 7, the concentration of the B3GNT3 polypeptide fragment exhibited correlation with neither of the measurement values of the existing ovarian cancer markers CA125 (a) and GAT (b). By contrast, as shown in FIG. 8, positive correlation was observed between the CA125 measurement value and the GAT measurement value with a correlation coefficient of 0.65. These results suggested that the measurement value of the B3GNT3 polypeptide fragment according to the present invention reflects a disease marker secreted under a mechanism different from that of the existing ovarian cancer markers.

Example 9: Combination with MGAT5B Measurement Value

The measurement value in a test subject-derived sample of the epithelial ovarian cancer marker B3GNT3 polypeptide fragment of the present invention obtained in Example 8 can be combined with the measurement value in the test subject-derived sample of an additional epithelial ovarian cancer marker based on a glycosyltransferase to thereby further enhance the true positive rate of epithelial ovarian cancer in the test subject. Thus, the concentrations of the B3GNT3 polypeptide fragment as well as the additional epithelial ovarian cancer marker glycosyltransferase MGAT5B polypeptide fragment were quantitatively measured from the samples of the test subjects described in Example 8.

(Method)

The results of Experimental Example 1 shown in Example 8 were used as the concentration of the B3GNT3 polypeptide fragment in the samples of the test subjects. The concentration of the MGAT5B polypeptide fragment was measured with a cutoff value of 4.0 ng/mL by sandwich CLEIA in the same way as in Example 8 using two anti-MGAT5B antibodies, i.e., the GT131-12 antibody for immobilization and the GT131-7 antibody for detection, specifically recognizing the MGAT5B polypeptide fragment. As mentioned above, the GT131-12 antibody is produced by the hybridoma GT131-12, and the GT131-7 antibody is produced by the hybridoma GT131-7. Since the measurement concentration region of MGAT5B is approximately 1/10 of that of B3GNT3, the respective obtained measurement values were statistically analyzed using "Concentration measurement value of the MGAT5B polypeptide fragment×10+ Concentration measurement value of the B3GNT3 polypeptide fragment".
(Results)

Figure 9:
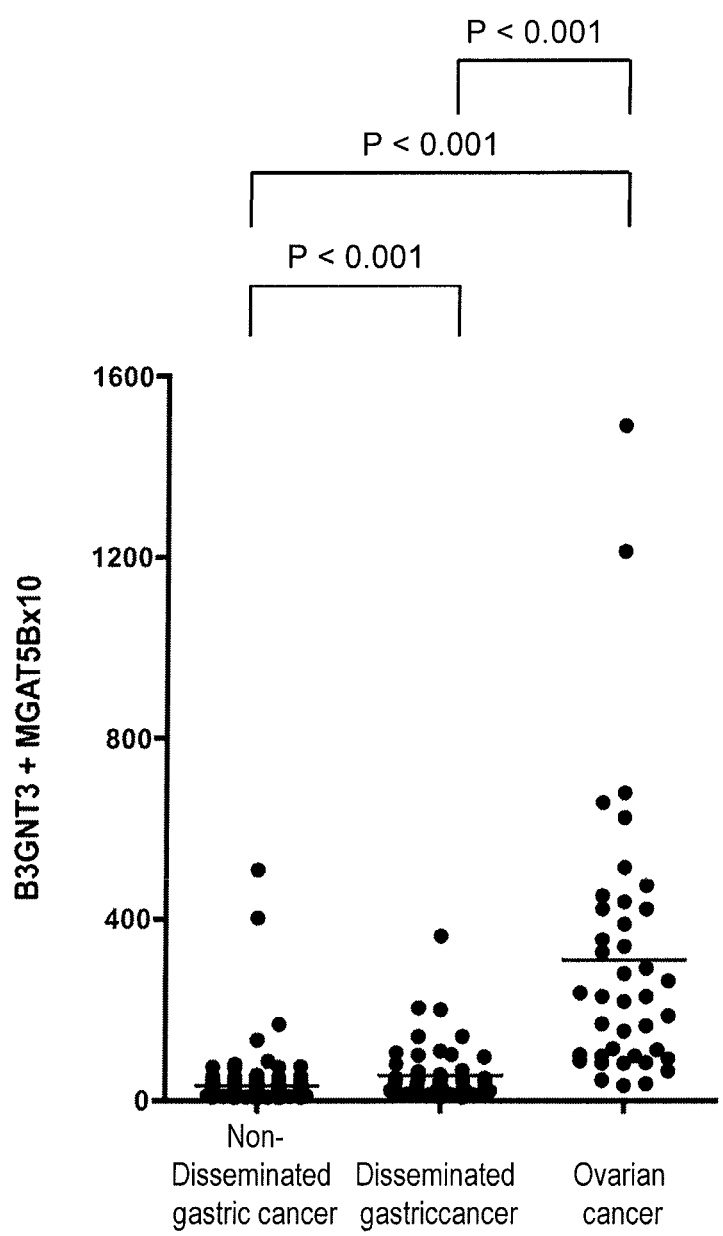
FIG. 9 shows indexed values of the combined concentrations of the epithelial ovarian cancer marker B3GNT3 polypeptide fragment of the present invention and an additional epithelial ovarian cancer marker MGAT5B polypeptide fragment in a peritoneal lavage fluid collected from a test subject, wherein the concentrations were measured by sandwich CLEIA using their respective specific antibodies.

The results are shown in FIG. 9. The ovarian cancer patient group exhibited distribution close to normal distribution as a whole with reduced false negative. Exceedingly high values exhibited by two gastric cancer patients were lowered by combination with the MGAT5B measurement value. Accordingly, the gastric cancer patient groups also exhibited the more unified distribution of measurement values. The statistical analysis resulted in larger significant difference (P<0.05→P<0.001) between the non-disseminated gastric cancer patient group and the disseminated gastric cancer patient group. Diagnosis efficiency at the optimal threshold point in the ROC curve of the ovarian cancer patient group vs. the disseminated gastric cancer patient group was improved from 65% to 74%.

All publications, patents, and patent applications cited herein are incorporated herein by reference in their entirety.
Deposition Number GT117-2; National Deposition No: FERM P-22095; International Accession No: FERM BP-11494

GT117-3; National Deposition No: FERM P-22096; International Accession No: FERM BP-11495

GT131-2; National Deposition No: FERM P-22097; International Accession No: FERM BP-11496

GT131-7; National Deposition No: FERM P-22098; International Accession No: FERM BP-11497

GT131-12; National Deposition No: FERM P-22099; International Accession No: FERM BP-11498

GT131-18; National Deposition No: FERM P-22100; International Accession No: FERM BP-11499

The invention claimed is:

1. A method for diagnosis of epithelial ovarian cancer comprising quantitatively detecting a β-1,3-N-acetylglucosaminyltransferase 3 polypeptide fragment and a β-1,6-N-acetylglucosaminyltransferase 5B polypeptide fragment present in a body fluid derived from a test subject, and
   determining that the test subject is diagnosed to be likely to have epithelial ovarian cancer when the detection results of the β-1,3-N-acetylglucosaminyltransferase 3 polypeptide fragment and the β1,6-N-acetylglucosaminyltransferase 5B polypeptide fragment are greater than a predetermined cut-off value,
   wherein the β-1,3-N-acetylglucosaminyltransferase 3 polypeptide fragment is detected using at least one antibody or antibody fragment selected from the group consisting of an antibody for detecting an epithelial ovarian cancer marker that recognizes as an epitope a part of a polypeptide consisting of the amino acid sequence of SEQ ID NO: 1; and a fragment of the antibody for detecting an epithelial ovarian cancer marker that recognizes as an epitope a part of a polypeptide consisting of the amino acid sequence of SEQ ID NO: 1, and
   wherein the predetermined cut-off value is 95 percentile of the detection results of the β-1,3-N-acetylglucosaminyltransferase 3 polypeptide fragment and the β1,6-N-acetylglucosaminyltransferase 5B polypeptide fragment in body fluid derived from normal individuals or patients other than epithelial ovarian cancer, and wherein the antibody is produced by a hybridoma identified by International Accession No. FERM BP-11494 or FERM BP-11495.

2. The method for diagnosis of epithelial ovarian cancer of claim 1, wherein the β-1,6-N-acetylglucosaminyltransferase 5B polypeptide fragment is detected using at least one antibody or antibody fragment selected from the group consisting of an anti-β-1,6-N-acetylglucosaminyltransferase 5B antibody recognizing as an epitope a part of a polypeptide consisting of the amino acid sequence of SEQ ID NO: 3, and a fragment of the anti-β-1,6-N-acetylglucosaminyltransferase 5B antibody, wherein the fragment specifically recognizes β-1,6-N-acetylglucosaminyltransferase 5B.

3. The method for diagnosis of epithelial ovarian cancer of claim 2, wherein the anti-β-1,6-N-acetylglucosaminyltransferase 5B antibody is produced by a hybridoma identified by International Accession No. FERM BP-11496, FERM BP-11497, FERM BP-11498, or FERM BP-11499.

4. A monoclonal antibody produced by a hybridoma identified by International Accession No. FERM ABP-11494 or FERM ABP-11495.

5. A hybridoma identified by International Accession No. FERM ABP-11494.

6. A hybridoma identified by International Accession No. FERM ABP-11495.

* * * * *